US011857568B2

(12) United States Patent
Mandler et al.

(10) Patent No.: US 11,857,568 B2
(45) Date of Patent: *Jan. 2, 2024

(54) TREATMENT AND PREVENTION OF ALZHEIMER'S DISEASE (AD)

(71) Applicant: Advantage Therapeutics, Inc., Fort Lauderdale, FL (US)

(72) Inventors: Markus Mandler, Fort Lauderdale, FL (US); Achim Schneeberger, Fort Lauderdale, FL (US); Wolfgang Zauner, Fort Lauderdale, FL (US); Arne Von Bonin, Fort Lauderdale, FL (US); Frank Mattner, Fort Lauderdale, FL (US); Walter Schmidt, Fort Lauderdale, FL (US)

(73) Assignee: Advantage Therapeutics, Inc., Fort Lauderdale, FL (US)

( * ) Notice: Subject to any disclaimer, the term of this patent is extended or adjusted under 35 U.S.C. 154(b) by 119 days.

This patent is subject to a terminal disclaimer.

(21) Appl. No.: 17/370,615

(22) Filed: Jul. 8, 2021

(65) Prior Publication Data

US 2022/0000908 A1    Jan. 6, 2022

Related U.S. Application Data

(63) Continuation of application No. 15/307,246, filed as application No. PCT/EP2015/059341 on Apr. 29, 2015, now Pat. No. 11,065,273.

(30) Foreign Application Priority Data

Apr. 29, 2014   (EP) ..................................... 14166355
Apr. 29, 2014   (EP) ..................................... 14166388

(51) Int. Cl.
*A61K 33/06*  (2006.01)
*A61K 33/08*  (2006.01)
*A61K 33/42*  (2006.01)
*A61K 45/06*  (2006.01)

(52) U.S. Cl.
CPC .............. *A61K 33/06* (2013.01); *A61K 33/08* (2013.01); *A61K 33/42* (2013.01); *A61K 45/06* (2013.01)

(58) Field of Classification Search
CPC ........ A61K 33/06; A61K 33/08; A61K 33/42; A61K 45/06
See application file for complete search history.

(56) References Cited

U.S. PATENT DOCUMENTS

| 6,743,427 B1 | 6/2004 | Schenk |
| 10,646,565 B2 | 5/2020 | Mandler et al. |
| 11,065,273 B2 | 7/2021 | Mandler et al. |
| 11,147,873 B2 | 10/2021 | Mandler et al. |
| 2003/0232758 A1 | 12/2003 | St. George-Hyslop |
| 2010/0028353 A1 | 2/2010 | Imbimbo |
| 2017/0049810 A1 | 2/2017 | Mandler et al. |
| 2017/0056495 A1 | 3/2017 | Mandler et al. |
| 2020/0338192 A1 | 10/2020 | Mandler et al. |
| 2022/0062412 A1 | 3/2022 | Mandler et al. |

FOREIGN PATENT DOCUMENTS

| CN | 1646559 A | 7/2005 |
| CN | 102834118 A | 12/2012 |
| JP | 2002/502802 A | 1/2002 |
| JP | 2017/514831 A | 6/2017 |
| JP | 2017/518275 A | 7/2017 |
| WO | WO-2011/120924 A1 | 10/2011 |

OTHER PUBLICATIONS

Devanand et al. "Hippocampal and entorhinal atrophy in mild cognitive impairment: Prediction of Alzheimer's disease." Neurology, Mar. 13, 2007, 68: 828-836. (Year: 2007).*
Lindblad, Erik. "Aluminium compounds for use in vaccines." Immunology and Cell Biology, 2004, 82: 497-505. (Year: 2004).*
"In Surprise, Placebo, not A.beta. Vaccine, Said to Slow Alzheimer's", retrieved from https://www.alzforum.org/news/research-news/surprise-placebo-not-av-vaccine-said-slow-alzheimers on Jan. 8, 2020.
Alhydrogel adjuvant 2%., retrieved online <http://www.invivogen.com/PDF/Alhydrogel_TDS.pdf>: 2 pages (2017).
Amber L. Clausi, et al. "Inhibition of Aggregation of Aluminum Hydroxide Adjuvant during Freezing and Drying," Journal of Pharmaceutical Sciences, vol. 97, No. 6, Jun. 2008, pp. 2049-2061.
Anne Corbett, et al., "Drug repositioning for Alzheimer's disease," Nature Reviews Drug Discovery, vol. 11, Nov. 2012, pp. 833-846.
Asher Mullard, "Sting of Alzheimer's failures offset by upcoming prevention trials," Nature Reviews Drug Discovery, vol. 11, Sep. 2012, pp. 657-660.
Bruno Dubois, et al., "Research criteria for the diagnosis of Alzheimer's disease revising the NINCDS-ADRDA criteria," Lancet Nuerol, vol. 6, Aug. 2007, pp. 734-746.
Christopher Exley, et al. "The immunobiology of aluminum adjuvants: how do they really work?" Elsevier, vol. 31, No. 3 (2010), pp. 103-109.
Combined Chinese Office Action and Search Report dated Feb. 2, 2019 in corresponding Chinese Patent Application No. 201580029850.7, 7 pages.
Committee for Medicinal Pioducts for Human Use (CHMP), "Guideline on Medicinal Products for the Treatment of Alzheimer's Disease and other Dementias," European Medicines Agency, Jul. 24, 2008, 19 pages.
D. Louis Collins, et al. "Automatic 3D Intersubject Registration of MR Volumetric Data in Standardized Talairach Space," Journal of Computer Assisted Tomography, vol. 18, No. 2, Mar./Apr. 1994, pp. 192-205.

(Continued)

*Primary Examiner* — Doan T Phan
(74) *Attorney, Agent, or Firm* — Foley Hoag LLP; Lucas P. Watkins; Alexander J. Chatterley

(57) ABSTRACT

The invention discloses an aluminium salt for use in the treatment and prevention of dementias associated with β-amyloid deposition, preferably AD.

19 Claims, 8 Drawing Sheets

Specification includes a Sequence Listing.

(56) References Cited

OTHER PUBLICATIONS

David Eliezer, "Amyloid Ion Channels: A Porous Argument or a Thin Excuse?" J. Gen. Physiol, vol. 128, No. 6, Nov. 27, 2006, pp. 631-633.
Derek C. Rogers, et al., "Use of SHIRPA and discriminant analysis to characterize marked differences in the behavioural phenotype of six inbred mouse strains," Rehavioural Brain Research, vol. 105, (1999) pp. 207-217.
Erik B Lindblad, "Aluminum adjuvants—in retrospect and prospect," Elsevier, vol. 22, (2004), pp. 3658-3668.
Erik B Lindblad, "Special Feature—Aluminum compounds for use in vaccines," Immunology and Cell Biology, vol. 82, (2004), pp. 497-505.
F. Aguilar, et al., Safety of aluminum from dietary intake—Scientific Opinion of the Panel on Food Additives, Flavourings, Processing Aids and Food Contact Materials (AFC), The European Food Safety Authority Journal, (2008), 122 pages.
Giovanni B. Frisoni, et al. "The clinical use of structural MRI in Alzheimer disease," Nat Rev Neurol, vol. 6 No. 2, Feb. 2010, pp. 1-24.
Hampel et al. The future of Alzheimer's disease: the next 10 years. Prog Neurobiol. Dec. 2011;95(4):718-28. Epub Nov. 22, 2011.
Harrison Measuring cognitive change in Alzheimer's disease clinical drug trials. J Nutr Health Aging. Jul.-Aug. 2007;11(4):327-9.
https://en.wikipedia.org/wiki/Phosphate-buffered_saline, retrieved May 29, 2017.
Jian Luo, et al. "Colony-stimulating factor 1 receptor (CSF1R) signaling in injured neurons facilitates protection and survival," The Journal of Experimental Medicine, vol. 210, No. 1, (2013), pp. 157-172.
Johanna Magga, et al. "Production of monocytic cells from bone marrow stem cells: therapeutic usage in Alzheimer's disease," Journal of Cellular and Molecular Medicine, vol. 16, No. 5, (2012) pp. 1060-1073.
Markus Mandler, et al., "Detection of Peri-Synaptic Amyloid-.beta. Pyroglutamate Aggregates in Early Stages of Alzheimer's Disease and A.beta.PP Transgenic Mice Using Novel Monoclonal Antibody," Journal of Alzheimer's Disease, vol. 28, (2012), pp. 783-794.
Markus Mandler, et al., "Tailoring the Antibody Response to Aggregated AII Using Novel Alzheimer's Vaccines," PLOS (7) One, Jan. 22, 2015, pp. 1-22.
Michael F. Powell et al., "Structure and Properties of Aluminum-Containing Adjuvants (Chapter 9)", Vaccine Design the Subunit and Adjuvant Approach, Dec. 31, 1995, pp. 249-250 (with cover pages).
Michael W. Weiner, et al., "The Alzheimer's Disease Neuroimaging Initiative: A Review of papers published since its inception," Alzheimers Dement, vol. 9, No. 5, Sep. 2013, pp. 1-160.
Nicholas Kozauer, et el., "Regulatory Innovation and Drug Development for Early-Stage Alzheimer's Disease," The New England Journal of Medicine, Mar. 28, 2013, pp. 1169-1171.
Nick C Fox, et al., "Using Serial Registered Brain Magnetic Resonance Imaging to Measure Disease Progression in Alzheimer Disease," Arch Nuerol, vol. 57, Mar. 2000, pp. 339-344.
Office Action as received in the corresponding JP Patent Application No. 2016-565334 dated Oct. 8, 2019 w/English Translation , citing documents , 8 pages w/translation.
P. Vemuri, et al., "MRI and CSF biomarkers in normal, MCI and AD subjects—Diagnostic discrimination and cognitive correlations," Neurology, vol. 73, Jul. 28, 2009, pp. 287-293.
P. Vemuri, et al., "MRI and CSF biomarkers in normal, MCI and AD subjects—Predicting future clinical change," Neurology, vol. 73, Jul. 29, 2009, pp. 294-301.
Paul S. Aisen, et al., "Moving towards early clinical trials for amyloid-targeted therapy in Alzheimer's disease," Nature Reviews Drug Discovery, Mar. 15, 2013, 3 pages.
Perrin et al. Multimodal techniques for diagnosis and prognosis of Alzheimer's disease. Nature Oct. 15, 2009;461(7266):916-22, Published online Oct. 14, 2009.
Philippa Marrauk, et al., "Towards an understanding of the adjuvant action of aluminum," Nat Rev Immunol, vol. 9, No. 4, Apr. 2009, pp. 1-16.
Puzzo et al. Behavioral assays with mouse models of Alzheimer's disease: practical considerations and guidelines. Biochem Pharmacol. Apr. 15, 2014;88(4):450-67. Epub Jan. 21, 2014.
Rajesh K. Gupta, "Aluminum compounds as vaccine adjuvants," Advanced Drug Delivery Reviews, vol. 32, (1998) pp. 155-172.
Robert A. Yokel, "The Toxicology of Aluminum in the Brain: A Review," NeuroToxicology, vol. 21, No. 5, (2000), pp. 813-828.
Schneeberger et al. Results from a Phase II Study to Assess the Clinical and Immunological Activity of AFFITOPE.RTM. AD02 in Patients with Early Alzheimer's Disease. J. Prev Alzheimers Dis. 2015;2(2):103-114.
Shannon L. Risacher, et al., "Neuroimaging and Other Biomarkers for Alzheimer's Disease: The Changing Landscape of Early Detection," Annu Rev Clin Psychol, vol. 9, (2013), pp. 1-31.
Steven C. Reed, et al., "Key roles of adjuvants in modern vaccines," Nature Medicine, vol. 19, No. 12, Dec. 2013, pp. 1597-1608.
Tarja Malm, et al., "The Role and Therapeutic Potential of Monocytic Cells in Alzheimer's Disease," GLIA, (2010), pp. 889-900.
Thomas A Comery, et al. "Acute .gamma.-Secretase Inhibition Improves Contextual Fear Conditioning in the Tg2576 Mouse Model of Alzheimer's Disease," The Journal of Neuroscience, vol. 25, No. 39, Sep. 25, 2005, pp. 8898-8902.
Vincent Boissonneault, et al., "Powerful beneficial effects of macrophage colony-stimulating factor on beta.-amyloid deposition and cognitive impairment in Alzheimer's disease," Brain A Journal of Neurology, vol. 132, (2009), pp. 1078-1092.
Yuri Sokolov, et al., "Soluble Amyloid Oligomers Increase Bilayer Conductance by Altering Dielectric Structure," The Journal of General Physiology vol. 128, No. 6, Nov. 13, 2006, pp. 637-647 plus cover page.

* cited by examiner

TREATMENT AND PREVENTION OF ALZHEIMER'S DISEASE (AD)

RELATED APPLICATIONS

This application is a continuation of U.S. patent application Ser. No. 15/307,246, filed Oct. 27, 2016, which is a U.S. National Stage Application of International Application No. PCT/EP2015/059341, filed Apr. 29, 2015, which claims priority to EP14166355.9, filed Apr. 29, 2014, and EP14166388.0, filed Apr. 29, 2014, the contents of each of which are fully incorporated by reference herein in their entireties.

SEQUENCE LISTING

The instant application contains a Sequence Listing which has been submitted electronically in ASCII format and is hereby incorporated by reference in its entirety. Said ASCII copy, created on Sep. 22, 2021, is named ATW-00102_SL.txt and is 835 bytes in size.

The present invention relates to means and methods for the treatment and the prevention of dementias associated with β-amyloid deposition, preferably Alzheimer's Disease (AD).

Various dementias are characterized by the aberrant accumulation of Amyloid-β polypeptides (Aβ) resulting in β-amyloid deposition. The most prominent form of β-Amyloidoses is AD. Other examples include but are not limited to Dementia with Lewy bodies and Dementia in Down syndrome.

AD is the most prevalent neurodegenerative disorder currently affecting 28 million people worldwide. It typically presents with a characteristic amnestic dysfunction associated with other cognitive-, behavioural- and neuropsychiatric changes. AD is characterized by the abnormal accumulation of intra- and extracellular amyloid deposits—closely associated with extensive astrocytosis and microgliosis as well as dystrophic neurones and neuronal loss. These amyloid deposits mainly consist of Aβ-peptides Aβ40 and Aβ42 derived from the Amyloid Precursor Protein (APP; gi:112927), which is expressed on various cell types in the nervous system. Aβ, peptides are considered to be directly involved in the pathogenesis and progression of AD.

Besides amyloid deposits, neurofibrillary tangles (NFT) embody the second characteristic neuropathological hallmark of AD, first described by Alois Alzheimer. These lesions occur in the hippocampus, amygdale association cortices, and certain subcortical nuclei. NFTs are located in the cytoplasm of neurons and are composed of hyperphosphorylated tau protein. Tau is an axonal, microtubule binding protein that promotes microtubule assembly and stability under normal conditions. Hyperphosphorylation of Tau results in loss of microtubule association and subsequent disassembly of microtubules, which in turn leads to an impairment of axonal transport and subsequent axonal and neuronal degeneration. It is still unclear whether tau hyperphosphorylation and tangle formation are a cause or a consequence of AD.

Besides amyloid and Tau/hyperphosphorylated Tau pathology, neuroinflammation can be considered as the third integral pillar of pathophysiologic changes causing neurodegeneration in AD. The neuroinflammatory phenotype in AD is characterized by robust and widespread activation of microglia and astrocytes in the affected brain regions, resulting in endogenous expression of proinflammatory cytokines, cell adhesion molecules, and chemokines. These changes are thought to result from glial reaction to events related to ongoing toxicity elicited by amyloid and Tau/hyperphosphorylated Tau and their mediators.

It is currently believed that one potential treatment strategy for AD and related disorders could be based on immunotherapy to prevent or reduce the accumulation of neurotoxic agents like Aβ, or Tau/hyperphosphorylated Tau.

Various active and passive treatment strategies targeting Tau/hyperphosphorylated Tau led to a reduction of Tau/hyperphosphorylated Tau deposition and associated neuropathological changes in animal models, however, no positive data in human AD patients are available so far. Quite in contrast, there have been a significant number of clinical trial failures in the most recent past: Results "from the Phase III clinical trials of two monoclonal antibodies—bapineuzumab and solanezumab—that target amyloid-β indicated little clinical benefit of immunological attack on amyloid-β at the dementia stage of sporadic disease" (Aisen et al., Nat. Rev. Drug Disc. 12 (2013), 324-325; Mullard, Nat. Rev. Drug Disc. 11 (2012), 657-660). Also other studies of hypothesis-driven candidate disease modifiers "such as anti-inflammatory drugs, secretase inhibitors and modulators, hormonal therapies, statins and other drugs have been disappointing", including the "clinical failure of the two leading γ-secretase inhibitors, semagacestat [ . . . ] and avagacestat" (Aisen et al., 2013; Mullard, 2012). Commentators have termed this poor clinical outcome of AD clinical trials as "the culmination of a 'lost decade' in Alzheimer's disease therapeutic trials, with no substantial success since the approval of memantine" (Aisen et al., 2013). In the course of this development, the US-FDA also amended the rules for approving new treatments for AD and recommended the use of AD specific biomarkers, such as radiologic biomarkers using PET (positron emission tomography) scans (Kozauer et al., N. Engl. J. Med. 368 (2013), 1170-1171).

WO 94/16327 A1 discloses therapeutic agents that involve an "amyloid protein ion channel". However, this concept of amyloid protein ion channel of WO 94/16327 A1 was not further prosecuted and was finally challenged scientifically (Sokolov et al., J. Gen. Physiol. 128 (2006), 637-647; commentary by Eliezer, J. Gen. Physiol. 128 (2006), 631-633).

In addition, the teachings of WO 94/16327 A1 imply an active interaction of Al-ions with potential Aβ-Ion channels in vivo, thereby inhibiting these channels. Thus, in order for aluminium to full fill this task, the compound has to reach the brain as the site of activity in the suggested concentrations. In the human brain normal levels of aluminium range from 0.25 to 0.75 mg/kg wet weight, with the grey matter (mainly responsible for regulating cognitive function affected in AD) containing about twice the concentration found in the white matter (The EFSA Journal (2008) 754, 24-88; Annex to the EFSA Journal (2008) 754, 1-34 opinion "Safety of aluminium from dietary intake"). There is evidence that with increasing age, aluminium concentrations may even increase in the human brain tissue. Similarly, several studies also indicate that brains derived from AD patients show higher Al-levels than healthy control brains (reviewed in Yokel, NeuroToxicology 21 (2000), 813-828). Thus the suggested therapeutically active Al concentration is already present in healthy and diseased brain (in the range of the intended use-formulation as described in WO 94/16327 A1, claim 12: 0.01-10 mg/kg). In addition, bioavailability of Al in brain after parenteral and oral uptake is kept low relying on actively regulated, highly efficient influx/efflux mechanisms and requires high peripheral doses to reach suggested therapeutic cerebral concentrations. It is therefore without plausible scientific basis that an additional increase in peripheral Al would lead to additional cerebral Al levels required for exerting direct, therapeutically beneficial effects without eliciting potential toxic effects.

Furthermore, FIGS. 7 and 8 of this application disclose that topically applied aluminium-oxyhydroxide is able to lower cognitive decline significantly in an APP-transgenic model for Alzheimer's disease (Tg2576) without significantly changing cerebral Aβ levels. This is implying an APP/Aβ independent mechanism underlying beneficial functional effects exerted by aluminium-oxyhydroxide in this AD model.

WO 99/27944 A1 discloses AD vaccines being essentially based on the presence of an agent effective to induce an immunogenic response against A. WO 2011/120924 A1 refers to an Aβ vaccine, which is essentially based on Aβ1-6 peptide bound to a virus-like particle. WO 2006/005707 A2, WO 2009/149486 A2 and WO 2009/149485 A2 disclose Aβ, mimotope peptides for use in vaccines for the prevention and treatment of AD.

Heneka et al. (Nature, 493 (7434) (2012): 674-678) suggest the treatment of AD by inhibition of NLRP3 in order to reduce amyloid-β aggregation. Aimanianda et al. (TIPS, 30 (6) (2009): 287-295) discloses that alum activates NLRP3.

Magga et al. (J. Cell. Mol. Med. 16 (2012): 1060-1073) report the production of monocytic cells from bone marrow stem cells and their therapeutic use in AD. Lebson et al. (Cell Transp. Cogn. Com. 17 (2008): 470/471) disclose monocyte gene therapy in AD APP+PS1 transgenic mice. WO 2012/055981 A1 suggests the use of a "TLR4 agonist free of endotoxin" for the prevention or reduction of amyloid deposition. Malm et al. (GLIA 58 (2010): 889-900) review the role and therapeutic potential of monocytic cells in AD.

WO 2009/105641 A1 discloses the use of M-CSF for the treatment of amyloidosis. Boissionneault et al. (Brain 132 (4) (2008): 1078-1092) report the effects of M-CSF on amyloid deposition and cognitive impairment in AD. Luo et al. (Neuroscience letters 367 (2) (2013): 210-172) disclose that Colony-stimulating factor 1 receptor (CSF1R) signalling in injured neurons facilitates protection and survival.

Accordingly, so far no effective, disease modifying treatment is available to stop the progressive neurodegeneration and associated cognitive decline in human patients. Available treatment modalities for AD include three acetylcholinesterase inhibitors (AChEI) and one N-Methyl-D-aspartate (NMDA) antagonist. Their effects are small and only symptomatic in nature (see e.g. Corbett et al., Nat. Rev. Drug Discov. 11 (2012), 833-846). Thus, there is a high medical need for a disease-modifying drug.

It is an object of the present invention to provide means and methods for the treatment and prevention of AD enabling a cure to AD in the meaning that the status of the diseased patient is not further developing or even ameliorated. Another object is to provide means and methods for preventing the development of AD in persons having or being at risk of developing AD. More specifically, it is an object of the present invention to provide efficient AD treatment, as proven with respect to at least one significant biomarker, as measured by brain imaging modalities using MRI (Magnetic resonance imaging) or emission tomography based techniques.

Therefore, the present invention provides an aluminium salt for use in the treatment and prevention of dementias associated with β-amyloid deposition, preferably Alzheimer's Disease (AD).

In the course of the present invention it has surprisingly turned out that aluminium salts as such have proven in clinical trials to be effective in providing real disease modifying effects in AD patients leading to clinical efficacy hitherto not seen in any of the clinical trials for AD medication so far. The present invention therefore provides a breakthrough technology for this disease. For the first time, a significant disease modifying effect could be detected in AD patients. Moreover, the present invention has also turned out to be effective without the significant side effects reported in other clinical trials for AD medication, especially in the field of AD immunotherapy.

More specifically, the present invention has achieved a statistically significant disease modifying effect in AD patients with respect to MRI scans of the volume of the (right) hippocampus. Moreover, for the first time, the correlation of a clinical biomarker and a radiologic biomarker has been shown in the course of clinical trials performed for the present invention. Structural MRI has been highlighted as a significant biomarker, in the most recent scientific literature (Risacher et al., Annu. Rev. Clin. Psychol. 9 (2013), 621-648; Vermuri et al., Neurology (2009), 287-293 and 294-301; Weiner et al., Alzh. Dememt. 9 (2013), e111-94; Frisoni et al., Nat. Rev. Neurol. 6 (2010), 67-77; Fox et al., Arch. Neurol. 57 (2000), 339-344).

MRI provides great power to effect cross-sectional groupwise discrimination and better correlation with general cognition and functional status cross-sectionally. MRI reflects clinically defined disease stage even better than various CSF biomarkers tested (Vermuri et al., Neurology 73 (2009), 287-293 and 294-301). Numerous studies have demonstrated significantly reduced hippocampal and entorhinal cortex (EC) volume, as well as reduced cortical thickness in the medial and lateral temporal cortex, parietal lobe, and frontal lobes, in patients destined to convert from MCI to probable AD (MCI-converters), up to two years prior to clinical conversion (Risacher et al., 2013).

Accordingly, this biomarker was investigated in the course of the clinical trials performed for the present invention in parallel with the standard clinical parameters (monitoring functional and cognitive function of AD patients).

With the present invention, a significant improvement in the development of AD patients compared to the usual development of AD patients (gradual cognitive, functional and behavioural decline) can be achieved so as to satisfy the long-felt need of providing a disease-modifying treatment of AD.

Accordingly, subject matter of the present invention is the use of an aluminium salt in the treatment and prevention of dementias associated with β-amyloid deposition, preferably AD, wherein an effective amount of such aluminium salt is administered to a patient suffering from the β-amyloid deposition or being at risk of developing a β-amyloid deposition, preferably a patient having or being at risk of developing AD, Dementia with Lewy bodies and Dementia in Down syndrome, especially AD.

Aluminium salts have a long-standing use as adjuvants in vaccines, however, during the years the pharmaceutical use of such salts has been reduced to mostly two suspension preparations, namely Alhydrogel (aluminium-oxyhydroxide) and AdjuPhos (aluminiumhydroxyphosphate), onto which antigens are adsorbed for vaccine preparations (reviewed in E. B. Lindblad (2004) Vaccine 22, 3658-3668; E.

B. Lindblad (2004) Immunology and Cell Biology 82, 497-505; R. K. Gupta (1998) Adv. Drug Delivery Rev. 32, 155-172).

Despite its long use, the mode of action of Alhydrogel as an adjuvant is poorly understood. The initial hypothesis, that Alhydrogel forms a depot at the injection side has turned out to be only one part of a multi-faceted story (reviewed in C. Exley, P. Siesjö, H. Eriksson (2010) Trends Immunol. 31, 103-109; S. L. Hem, H. HogenEsch (2007) Expert Rev. Vaccines 6, 685-698; P. Marrack, A. S. McKee, M. W. Munks (2009) Nature Rev. Immunol. 9, 287-293; S. G. Reed, M. T. Orr, C. B. Fox (2013) Nat. Med. 19, 1597-1608).

The main presentations of aluminium adjuvants used in humans are aluminium hydroxide (or aluminium oxyhydroxide) and aluminium phosphate. Both presentations are usually prepared by exposing a soluble aluminium salt (historically potassium alum, i.e. $KAl(SO_4)_2.12H_2O$, was often used) to alkaline conditions, upon which a suspension is formed. Characterisation with X-ray crystallography and IR spectroscopy revealed a boehmite-like structure (aluminium oxyhydroxide) for aluminium hydroxide and an amorphous structure corresponding to aluminium hydroxyphosphate for aluminium phosphate.

Therefore, preferred aluminium salts according to the present invention have the general formula $Me_a^+Al_b^{3+}An^{c-}.nH_2O$, wherein $Me^+$ is $Na^+$, $K^+$, $Li^+$, $Rb^+$, $Cs^+$ or $NH_4^+$;
An is $PO_4^{3-}$, $SO_4^{2-}$, $O(OH)^{3-}$, $O_2^-$ or $OH^-$;
a is 0, 1, 2, or 3;
b is 1 or 2;
c is 1, 2, 3, 4, 5, or 6; and
n is 0 to 48.

Preferred examples of such aluminium salts are those that have been studied, examined and verified in and for human use, such as aluminium hydroxide, aluminium oxyhydroxide, aluminium phosphate, aluminium sulphate, or any kind of "alum" (wherein "alum" is usually referred to a class of chemical compounds, including the "classical alum", a hydrated potassium aluminium sulfate (potassium alum) with the formula $KAl(SO_4)_2.12H_2O$, and—more generally double sulfate salts, with the formula $AAl(SO_4)_2.12H_2O$, where A is a monovalent cation such as potassium or ammonium).

The most preferred embodiments of the aluminium salts according to the present invention are selected from aluminium hydroxide, aluminium oxyhydroxide, aluminium phosphate, or aluminium sulphate, especially aluminium oxyhydroxide, which has been intensively investigated in the course of the present invention, since it is the preferred adjuvant in human use (as Alhydrogel adjuvant in various vaccines).

The aluminium salt according to the present invention may be admixed with other substances to achieve the disease-modifying effects according to the present invention. However, since the aluminium salts according to the present invention have also a protein binding capacity (also depending on the pI of the protein and the pH of the pharmaceutical preparation), the aluminum salt concentrations have to be increased when proteins or polypeptides are present in the pharmaceutical preparation to be administered to a patient.

For example, aluminium phosphate (Adju-Phos) has a maximal binding capacity (in mg protein/mg aluminum at pH 7.4) to Lysozyme (pI 11.0) of 1.4±0.1; aluminium oxyhydroxide (Alhydrogel) to Ovalbumin (pI 4.6) of 1.6±0.1 and to BSA (pI 4.9) of 2.2±0.1 (Jones et al., JBC 280, (2005), 13406-13414). In order to account for the aluminium that is bound to such proteins, more aluminium salt has to be provided in such admixed pharmaceutical preparations than in preparations that contain the aluminium salt as the single effective ingredient or—at least in the absence of proteins or polypeptides in the pharmaceutical preparation. For example, if a pharmaceutical composition according to the present invention should provide the effectiveness of a dose of 2 mg aluminium salt, especially aluminium oxyhydroxide, and contains a specific amount of proteins or polypeptides which binds to the aluminium salt, an amount equal to the aluminium salt portion binding to such proteins has to be additionally included in the pharmaceutical preparation to provide 2 mg "free" aluminium salt.

It is therefore preferred to administer the aluminium salt according to the present invention contained in a pharmaceutical preparation, wherein this preparation contains the aluminium salt, especially aluminium oxyhydroxide, as the single effective ingredient.

The most preferred embodiment of the present invention comprises the effective administration of aluminium oxyhydroxide (particularly as Alhydrogel) to AD patients.

Aluminium oxyhydroxide preparations have a point of zero charge at a pH of ~pH 11, while aluminium hydroxyphosphate might have a point of zero charge as low as pH 4 (depending on the phosphate content). Therefore aluminium oxyhydroxide and aluminium hydroxyphosphate have an opposite surface charge at neutral pH, with the latter being negatively charged. It has to be mentioned, however, that the surface charge may change depending on the exact buffer composition, especially phosphate ions have the capacity to lower the surface charge of aluminium oxyhydroxide.

For aluminium oxyhydroxide, the preparation is devoid of anions such as sulphates, nitrates, or chlorides and has a specified heavy metal content of less than 20 ppm. The suspension of aluminium oxyhydroxide has a particle size distribution between 2 μm and approximately 10 μm, which are aggregates composed of smaller fibers of ~2 nm×4.5 nm×10 nm.

According to this most preferred embodiment, the current invention relates to the use of European Pharmacopoeial grade (Aluminium-oxyhydroxide, monograph 1664), more specifically to the product manufactured by Brenntag Biosector (2% Alhydrogel) tested towards EP compliance. Alhydrogel is available in three varieties: Alhydrogel 1.3%; Alhydrogel 2% and Alhydrogel "85". Alhydrogel 2% was elected as the International Standard Preparation for aluminium hydroxide gels. The pharmaceutical preparation according to the present invention is aseptically formulated into a suitable buffer, preferably an isotonic phosphate buffer (1 mM to 100 mM), preferably at a concentration of ≥1.0 mg/ml Alhydrogel (given as $Al_2O_3$ equivalent; this metric (Al as "$Al_2O_3$ equivalent") is used generally for the present invention; accordingly, all doses and amounts referred to in the present application, as far they are relating to aluminum salts (especially as far as they are relating to aluminium oxyhydroxide) refer to $Al_2O_3$ equivalents (of aluminium oxyhydroxide (Alhydrogel))), even more preferably at a concentration of ≥1.5 mg/ml Alhydrogel (given as $Al_2O_3$ equivalent), most preferable at a concentration of ≥2.0 mg/ml Alhydrogel (given as $Al_2O_3$ equivalent). The amount of aluminium salt for Alhydrogel is given as $Al_2O_3$ equivalent in line with the strength as stated by the manufacturer (i.e. 2% Alhydrogel equates to 2% $Al_2O_3$, i.e. 20 mg/mL). This concentration is directly convertible into the respective concentration of aluminium by using the respective molecular masses (20 mg/mL $Al_2O_3$(Mw 101.96) corresponds to 10.6 mg/mL aluminium (molecular mass 26.98)). Depending on the salt used this value cam easily be converted into the necessary amount/concentration of a different aluminium salt (it is clear that these values are based solely on the amount of aluminium (salt), and other aspects, such as the contribution of the particulate nature of Alhydrogel is not taken into account.

Alhydrogel 2%, often also referred to as alum, is an aluminium oxyhydroxide wet gel suspension.

In the most preferred embodiment of the present invention, the aluminium salt to be administered to the AD patient is an aluminium oxyhydroxide suspension, preferably European Pharmacopoeia grade aluminium-oxyhydroxide (monograph 1664), especially Alhydrogel. The aluminium oxyhydroxide is administered in an amount effective to achieve an AD ameliorating effect, as defined by the EMEA Guideline on medical products for the treatment of AD and other dementias (Document Ref. CPMP/EWP/553/95 Rev.1 of 24 Jul. 2008). Accordingly, any administration procedure or dosage regimen for the aluminium salt formulation, especially aluminium-oxyhydroxide formulation, according to the present invention that is suitable to achieve the AD modifying effect as provided by the present invention is subject to the present invention. Although it is possible to deliver the preparation according to the present invention by way of slow infusion, the preferred strategy for administration is by administration of doses, for example by subcutaneous injection. Preferably, therefore the administration dose of the aluminium salt, preferably aluminium oxyhydroxide, is of at least 1.2 mg to an AD patient. A preferred range of amount to be administered to a patient is an amount of the aluminium salt, preferably aluminium oxyhydroxide, of 1.2 mg to 5.0 mg. The AD ameliorating effect of the aluminium salt, preferably aluminium oxyhydroxide, administration is even more pronounced at an amount of at least 1.5 mg. According to another preferred embodiment the aluminium salt, preferably aluminium oxyhydroxide, is administered in an amount of 1.5 mg to 5.0 mg, preferably 1.5 to 3.0 mg, especially 1.5 to 2.5 mg, to an AD patient. Another preferred embodiment comprises administration of the aluminium salt, preferably aluminium oxyhydroxide, in an amount of 1.6 mg to 2.5 mg, preferably 1.8 to 2.2 mg, especially 1.9 to 2.0 mg, to an AD patient.

According to another preferred embodiment, the aluminium salt, preferably aluminium oxyhydroxide, is administered in amount of 2.2 mg or higher. This amount is even higher as prescribed in the US general biological products standards (U.S.C. 21 CFR 610.15 (as of 1 Apr. 2013)). Such preferred higher ranges of the aluminium salt, preferably aluminium oxyhydroxide, are i.a. 2.2 to 10 mg, 2.2 to 8 mg, 2.2 to 5 mg, and 2.2 to 4 mg for one administration dose.

Preferably, the aluminium salt is the single effective substance to be applied in the administration dose. The aluminium salt preparation according to the present invention may, however, contain various auxiliary substances that have no specific clinical effect but are useful in the dosage form to be administered, be it for administration purposes, storage purposes, or other purposes. According to a preferred embodiment, the aluminium salt preparation, preferably the aluminium oxyhydroxide preparation, to be applied according to the present invention contains a pharmaceutically acceptable carrier, diluent or excipient, for example water for injection. Preferably, the aluminium salt preparation, especially the aluminium oxyhydroxide preparation, according to the present invention additionally contains one or more stabilisators, especially thiomersal, detergents, antioxidants, complexing agents for mono- or divalent metal ions, especially ethylenediaminetetraacetic acid (EDTA), sugars, sugar alcohols, glycerol, and/or buffer substances, especially TRIS or phosphate buffer substances. This, of course, also includes mixtures of such auxiliary substances.

The dosage form to be administered to the patients can be provided in any convenient volume, preferably as injectable suspension, e.g. with a volume of between 0.1 and 10 ml, more preferred of 0.2 to 5 ml, especially of 0.4 to 3 ml. Specifically preferred volumes are 0.5, 1, 1.5 and 2 ml. The pharmaceutical preparations according to the present invention are produced according to pharmaceutical Good Manufacturing Practice (GMP), as required and defined by the European and/or US Pharmacopeia.

According to a preferred embodiment, the aluminium salt, preferably the aluminium oxyhydroxide, is administered to a patient in a suspension with a pH of 4 to 10, preferably of 5 to 9, more preferred of 6 to 8, especially from 7.0 to 7.5. Preferably, the suspension is an isotonic suspension.

Preferably, the aluminium salt is administered by a route that is as convenient as possible for the AD patient but is still effective to achieve an AD modifying effect. Most effective treatment routes of the aluminium salt, preferably aluminium oxyhydroxide, according to the present invention are subcutaneous, intranodal, intradermal, or intramuscular administration, especially subcutaneous administration. Subcutaneous administration is performed as a bolus into the subcutis, the layer of skin directly below the dermis and epidermis, especially in the fatty tissue in the subcutis.

Administration regimes can be optimised individually for each AD patient, depending on the treatment success, as measured by various parameters, especially by cognitive and functional performances and by biomarkers, especially structural MRI concerning hippocampus volume (see below). In the course of the clinical trials conducted for the present invention, at least monthly administrations of the aluminium salt, preferably aluminium oxyhydroxide, to an AD patient have proven to be successful in ameliorating AD. In order to achieve a long lasting therapeutical effect, such at least monthly administrations should be continued for at least three months, especially at least six months.

Administration of the aluminium salt, preferably aluminium oxyhydroxide, according to the present invention may also be performed at least twice a month (for example bi-weekly or weekly); also in such a dosage regimen, the aluminium salt, preferably aluminium oxyhydroxide, should be administered to an AD patient at least for a period of three months, preferably for at least six months, more preferred for at least twelve months, especially at least 24 months.

According to a preferred embodiment the aluminium salt, preferably aluminium oxyhydroxide, is administered to an AD patient subcutaneously in the (outer area of the) upper arm, preferably alternating in the left and in the right upper arm (i.e. administering the first dose into the right (or left) upper arm and the second dose into the left (right arm), and so on). Other convenient (or alternative) areas for subcutaneous administration are just above and below the waist (except the area right around the navel (a 2-inch circle)), the upper area of the buttock, preferably just behind the hip bone, the front of the thigh, midway to the outer side, 4 inches below the top of the thigh to 4 inches above the knee, etc.

Alternatively, the dose to be administered can also be split into two (or more) split doses that are administered simultaneously (at the same physician date; at least at the same day) to the AD patient. For example, a dose of 2 mg may be split to split doses of 1.8 and 0.2 mg, 1.7 and 0.3 mg, 1.5 and 0.5 mg, 1.34 and 0.76 mg, 1.0 and 1.0 mg, 1.05 and 0.95 mg, 1.0, 0.5 and 0.5 mg, 0.6, 0.6 and 0.7 mg, 0.2, 0.5, and 1.3 mg, 0.5, 0.5, 0.5 and 0.5 mg, 0.2, 0.3, 0.5 and 1.0 mg, etc. The split doses may be administered at different administration sites or, preferably, at the same site of administration. The "same site of administration" is within an area of 10 cm$^2$ of the skin, preferably within an area of 5 cm$^2$ of the skin, especially within 1 cm$^2$ of the skin. Preferred split doses contain the aluminium salt, preferably aluminium oxyhydroxide, in an amount of 0.8 to 5.0 mg, preferably of 1.0 to 3.0, especially from 1.0 to 1.5 mg.

In order to achieve a very long lasting effect of the AD amelioration, the treatment according to the present invention is performed for longer than one year. According to a preferred embodiment of the present invention, the aluminium salt is administered at least monthly for at least two years, preferably at least four years, especially at least 8 years, to an AD patient.

Administration of the aluminium salt, preferably the aluminium oxyhydroxide, according to the present invention may be performed by any suitable administration device. For convenience reasons, the aluminium salt dose, preferably the aluminium oxyhydroxide dose, is administered by an injection device, especially a syringe, to an AD patient. The pharmaceutical preparations for use in the present invention can be provided in any suitable form. Preferably, they are provided in a storage stable form. Storage stability can be assured by various means, such as sterilisation, addition of stabilisers, freezing, lyophilisation, etc. Preferably, combinations of such means are used to enhance storage stabilities of such preparations. When aluminum-salt agents, such as aluminium oxyhydroxide are frozen or lyophilized, an aggregation of adjuvant particles during processing may be observed. By cooling such formulations, especially aluminium oxyhydroxide (Alhydrogel) formulations, at faster rates or by the addition of sufficient amounts of a glass forming excipient, such as trehalose, aggregation of Alhydrogel, can be prevented or minimized. It was proposed that freeze-concentration of buffer salts induces modifications in surface chemistry and crystallinity of such aluminium agents, which in turn favour aggregation. These modifications and the resulting aggregation of such Alhydrogel particles can be excluded or minimized through choice of buffer ions, or kinetically inhibited by rapidly forming a glassy state during freezing (see e.g. Clausi et al., J Pharm Sci. 2008 June; 97(6):2049-61).

The pharmaceutical compositions to be applied to AD patients according to the present invention are manufactured (and finished) into suitable containers, and sold for example in sealed vials, ampoules, cartridges, flexible bags (often constructed with multi-layered plastic), glass or polypropylene bottles or, preferably, in syringes, especially in prefilled (ready-to-use or ready-to-reconstitute) syringes.

According to a preferred embodiment of the present invention, the aluminium salt, preferably the aluminium oxyhydroxide, is administered in an amount of at least 1.8 mg to an AD patient.

Preferred patients to which the aluminium salt preparations, preferably aluminium oxyhydroxide preparations, according to the present invention is administered are AD patients that are early stage patients, including those patients that are often also referred to as "patients with mild cognitive impairment" (MCI). The concept of MCI was developed in the 1990s to capture patients with early clinical signs of Alzheimer disease (AD) who did not yet fulfil the criteria for dementia. The amnestic variant of MCI features the following: memory complaints, preferably qualified by an informant; memory impairment for age, as indexed by low cognitive performance in one or more neuropsychological tests that tap into learning abilities (for example, prose recall, word list); preserved general cognitive function (for example, Mini-Mental State Examination score of 24 out of 30 or above); intact activities of daily living; and no dementia. About two-thirds of all patients with amnestic MCI harbour the pathological features of AD and develop the clinical syndrome of Alzheimer dementia within 5 years, whereas the remaining one-third have non-progressive or very slowly progressive causes of cognitive impairment (for example, depression or age-related cognitive impairment). Proposed new diagnostic criteria for AD developed in 2007 (Dubois et al., Lancet Neurol. 6 (2007), 734-746) suggested that the disease can be recognized at the MCI stage if the patient is positive for at least one of the following four markers: medial temporal atrophy on MRI; temporoparietal cortical hypometabolism on 18F-fluorodeoxyglucose PET; abnormality of cerebrospinal fluid markers (tau, amyloid-β42 or phospho-tau); and positivity on amyloid imaging with PET. This patient population is not only included in the AD patients to be treated according to the present invention, it is a specifically preferred group of patients for which the treatment method according to the present invention is specifically effective. This is in line with the revised criteria for AD clinical trials adopted by the US-FDA (Aisen et al., 2013; Kozauer et al., 2013). Accordingly, it is preferred to treat patients in an early state of AD, as defined by a relatively high MMSE (mini-mental state examination or Folstein test) score. Preferably the AD patient to be treated according to the present invention is a patient with an MMSE score of between 23 and 30 (30 being the maximum), preferably between 24 and 30, more preferably between 25 and 29, especially between 26 and 29. Other preferred patient groups are patients greater than or equal to 27 points (indicating a normal cognition), 25 to 27 (slightly below normal cognition) or 19 to 24 (mild points cognitive impairment).

Early stage AD patients can also be selected by other scores, preferably scores that combine cognitive and functional parameters (and numerical limits) for limiting AD population to be (effectively treated), such as ADAS-cog, etc.

The present invention provides for the first time an AD treatment that is disease modifying. The effectiveness of the treatment according to the present invention is proven by the parameters required by the drug authorisation authorities, especially the EMEA and the US-FDA. For example, the EMEA guideline for AD treatment requires primary endpoints reflecting the cognitive and the functional domain. Accordingly, a combined (Composite) score is used for the clinical assessment of the present invention. This composite score combines two established scores, one for the cognitive function (ADAS-cog (Alzheimer's Disease Assessment Scale-cognitive subscale)) and one for the functional ability (ADCS-ADL (Alzheimer's Disease Co-operative Study-Activities of Daily Living Inventory)). The adapted ADAS-cog combines items that assess cognitive function. The adapted ADCS-ADL includes items that are sensitive to functional ability. Cognitive skills are expected to decline toward the beginning of the disease and one's ability to perform basic functions are expected to decline later in the disease. The combined primary outcome (Composite score according to the present invention) combines both the adapted ADAS-cog and adapted ADCS-ADL to create a composite that is sensitive to decline in cognitive and basic functions. The following equation is used to derive the combined primary outcome, i.e. combined composite:

Combined composite according to the present invention: =1.67*Word recall+1.35*Orientation+1.42*Word Recognition+0.55*Recall Instructions+0.81*Spoken Language+1.01*Word Finding+5.42*ONB+0.15*VPAL+0.19*Category Fluency+0.28*Belongings+0.35*Shopping+0.23*Hobbies+0.38*Beverage+0.37*Meal+0.23*Current Events+0.26*TV+0.33*Keeping Appointments+0.37*Travel+0.33*Alone+0.35*Appliance+0.49*Clothes+0.36*Read+0.62*Telephone+0.33*Writing Furthermore, AD biomarkers were observed with the present invention that are characteristic for AD development. EMEA and FDA criteria recommend newer techniques, such as MRI, especially atrophy of entorhinal or (para-) hippocampal cortex. With the present invention, PET (Positron emission tomography)-MRI was applied. More specifically, volume of right hippocampus (important for learning and memory of material that is difficult to verbalise) is used according to the present invention as significant AD biomarker for treatment success.

According to the present invention, a clinical effect in AD treatment can be observed which can be measured by a reduction in cognitive and/or functional decline (over a treatment period of about one year) by at least 30% (calculated by the score decline), preferably by at least 50%, especially by at least 70%, compared to a normal development of decline in AD patients. Preferably, cognitive and functional parameters remain essentially unchanged during treatment. This can be achieved by the present invention especially in patients with earliest stage patients (as suggested and recommended by the guidelines of EMEA and FDA), for example AD patients with MMSE of 23 or higher, preferably of 24 or higher, more preferred of 25 or higher, especially of 26 or higher. For those patients, Composite score change during treatment according to the present invention was still around the initial score after 18 months. This is significantly more than the minimum requirements for "disease modifying effects" as required by the EMEA ("From a regulatory point of view, a medicinal product can be considered as disease modifying, if the progression of the disease as measured by cognitive and functional assessment tools is reduced or slowed down and if these results are linked to an effect on the underlying disease process"; "a disease modifying effect will be considered when the pharmacologic treatment delays the underlying pathological or pathophysiological disease processes and when this is accompanied by an improvement of clinical signs and symptoms of the dementing condition").

The invention is further explained by way of the following examples and the figures, yet without being limited thereto.

Figure 3:
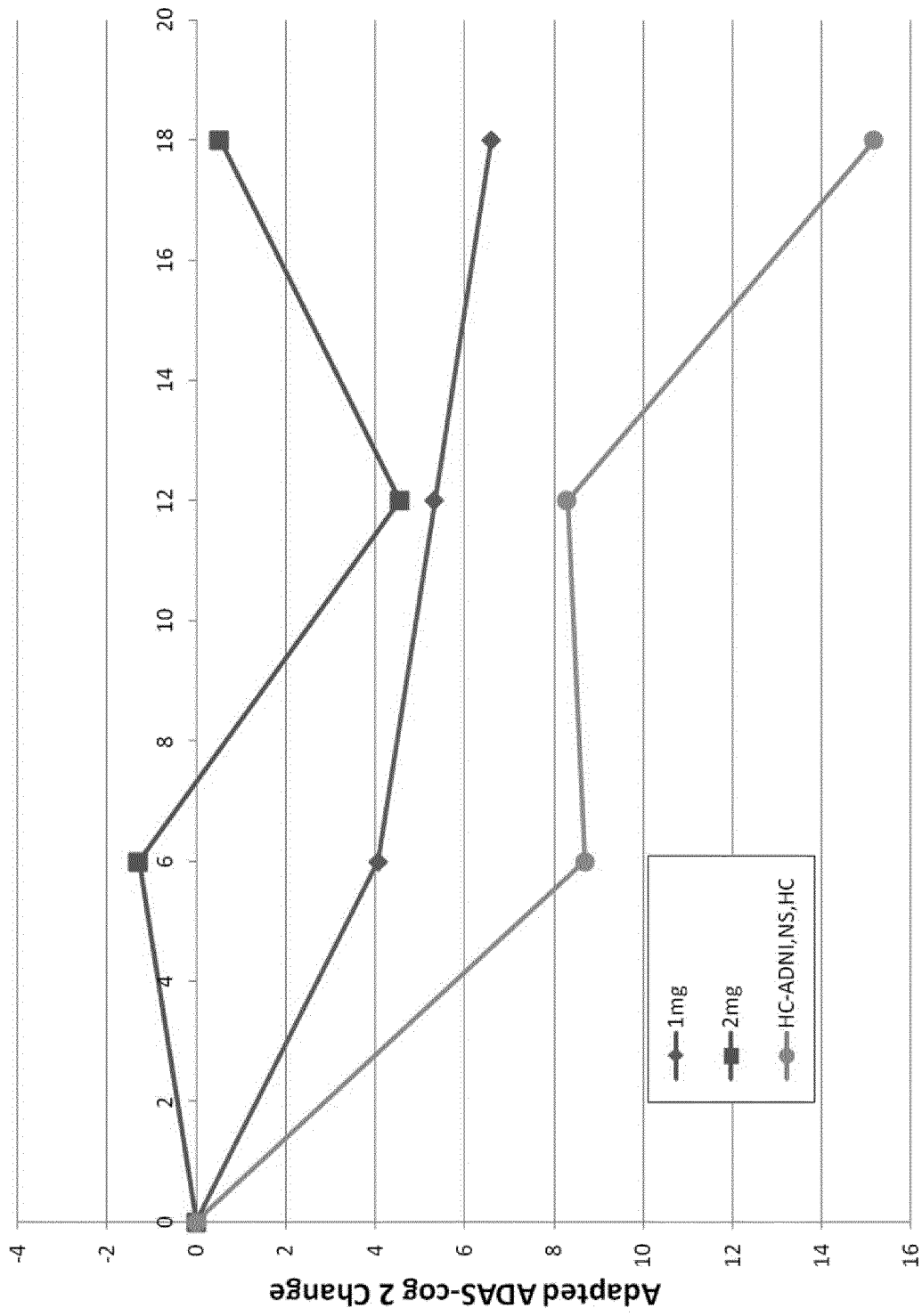

FIG. 3 shows slowing of disease progression apparent in the 2 mg and 1 mg aluminium group as evidenced by Adapted ADAS-cog (ADAS-cog items only; Least Squares Means) for the 1 mg and 2 mg aluminium oxyhydroxide group compared to the historical control (p-values: 1 mg vs. HC-ADNI,NS,HC: <0.0001; 2 mg vs. HC-ADNI,NS,HC: <0.0001).

Figure 4:
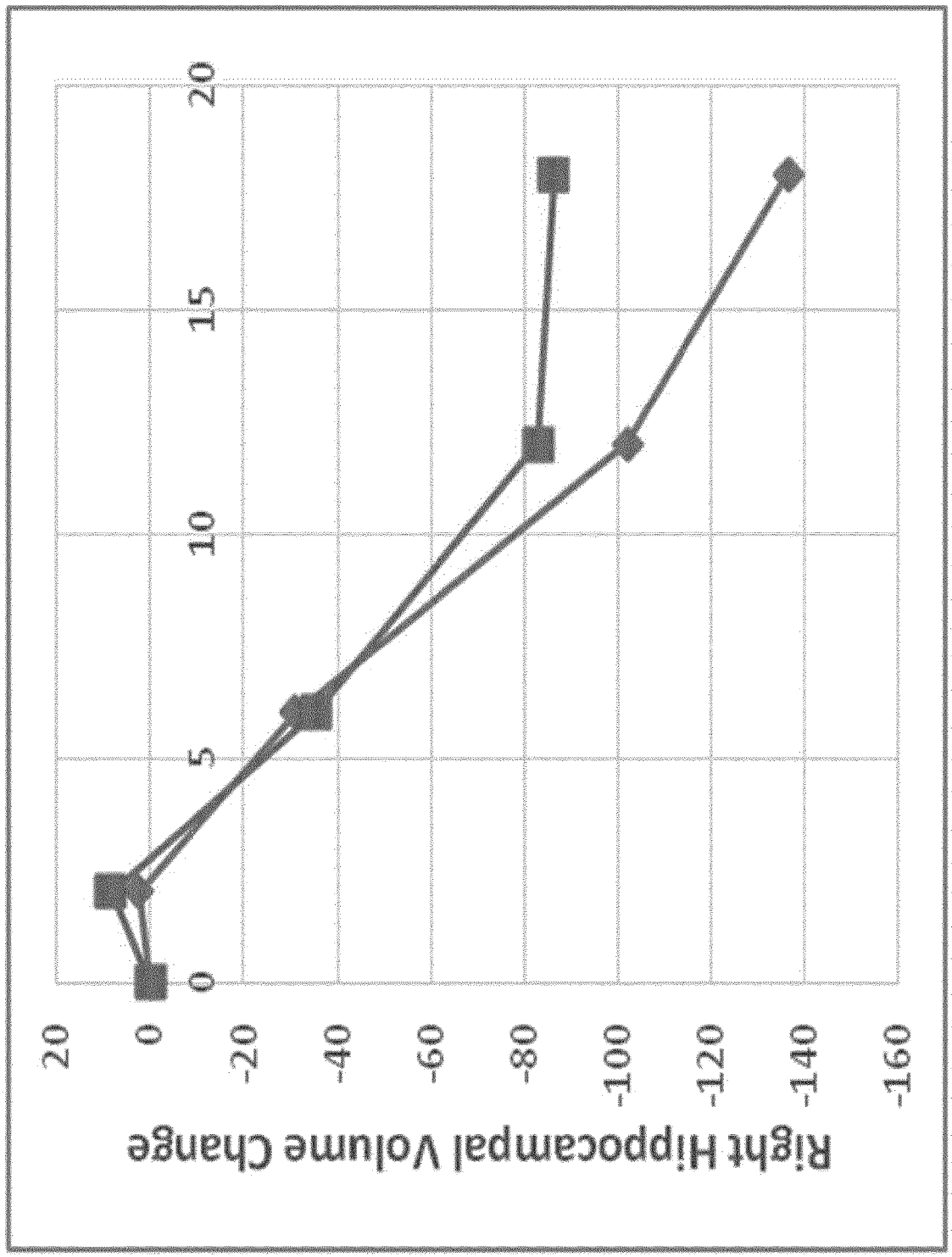

FIG. 4 shows development of volume (in $mm^3$) of right hippocampus for 2 mg and 1 mg aluminium oxyhydroxide treatment group of the mild population of patients (the mild population is defined by a baseline MMSE score of 24 and higher), showing that this effect is most pronounced in the cohort of patients in earlier disease stages.

Figure 5:
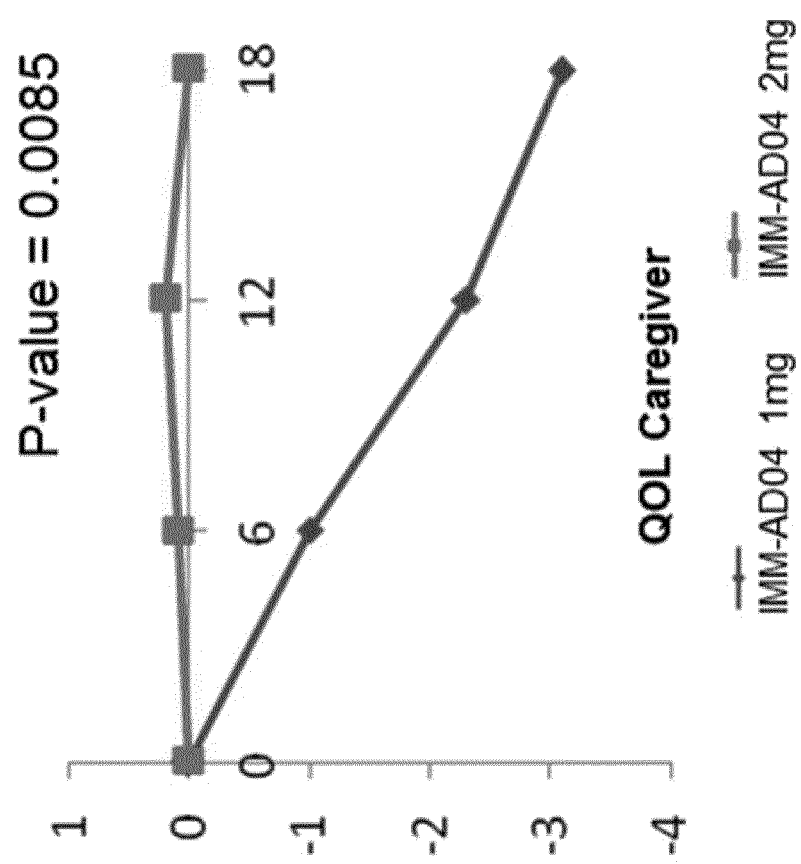

FIG. 5 shows the Quality of Life-Alzheimer's disease (QOL-AD) for caregivers. Caregivers completed the measure as a questionnaire about their patients' QOL. The measure consisted of 13 items, rated on a 4 point scale, with 1 being poor and 4 being excellent. Outcomes are shown as the change over time using a least squares means from a mixed model.

Figure 6:
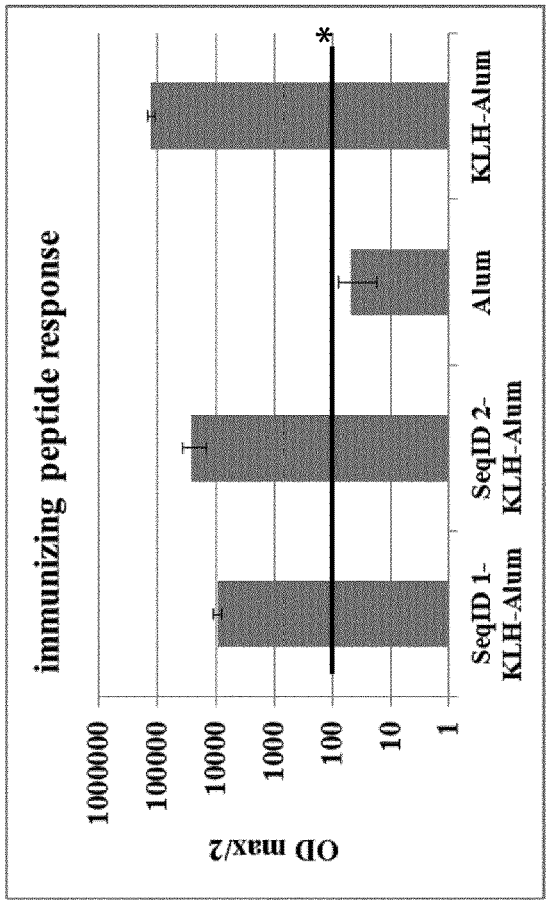
Figure 6:
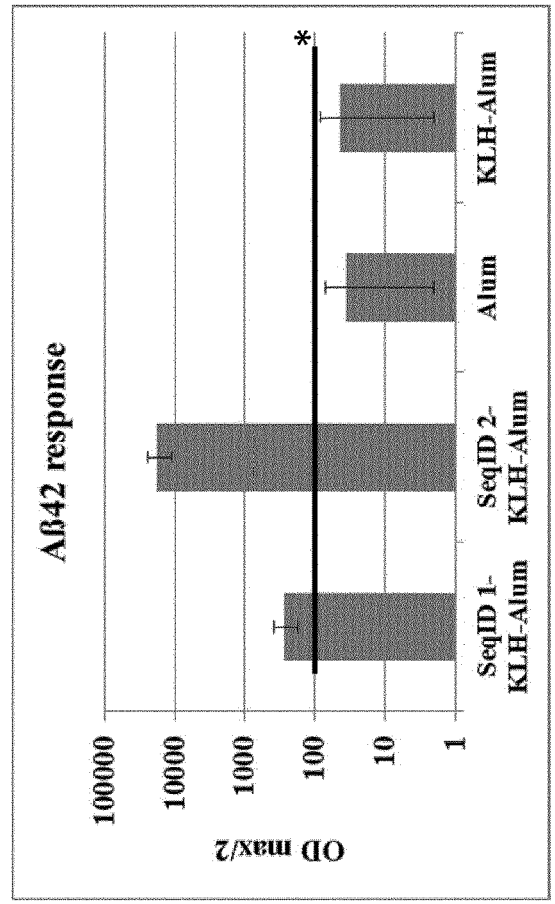

FIG. 6 shows immune response of the mice tested in the Tg2576 animal model: Tg2576-mice were injected 6×, s.c., at 4-week intervals with either conjugate-vaccine containing 30 µg net peptide, KLH formulated with Alum or Alum only. Alum doses used were equivalent to 2 mg/ml. Vaccination induced Abs were measured in plasma samples taken at sacrification (SeqID 1 (n=10), SeqID (n=8), KLH-Alum (n=10) and Alum only (n=8)). Samples were analyzed for their concentration of IgG Abs against specific peptides. Values depicted are the titer calculated as OD max/2 (at 405 nm) plus SEM. IgG response torwards the respective immunizing peptide (SeqID 1: anti SeqID 1; SeqID 2: anti SeqID 2, KLH-Alum: anti KLH, Alum: anti AD02); B) Reactivity towards human Aβ1-40/42 after immunization. SeqID 1 (n=10) and SeqID 2 (n=8), treated animals show anti Aβ40/42 reactivity, KLH-Alum and Alum only treated animals do not show reactivity above background. Background for this assay was set to 1/100, indicated by black lines and an asterisk in A+B.

Figure 7:
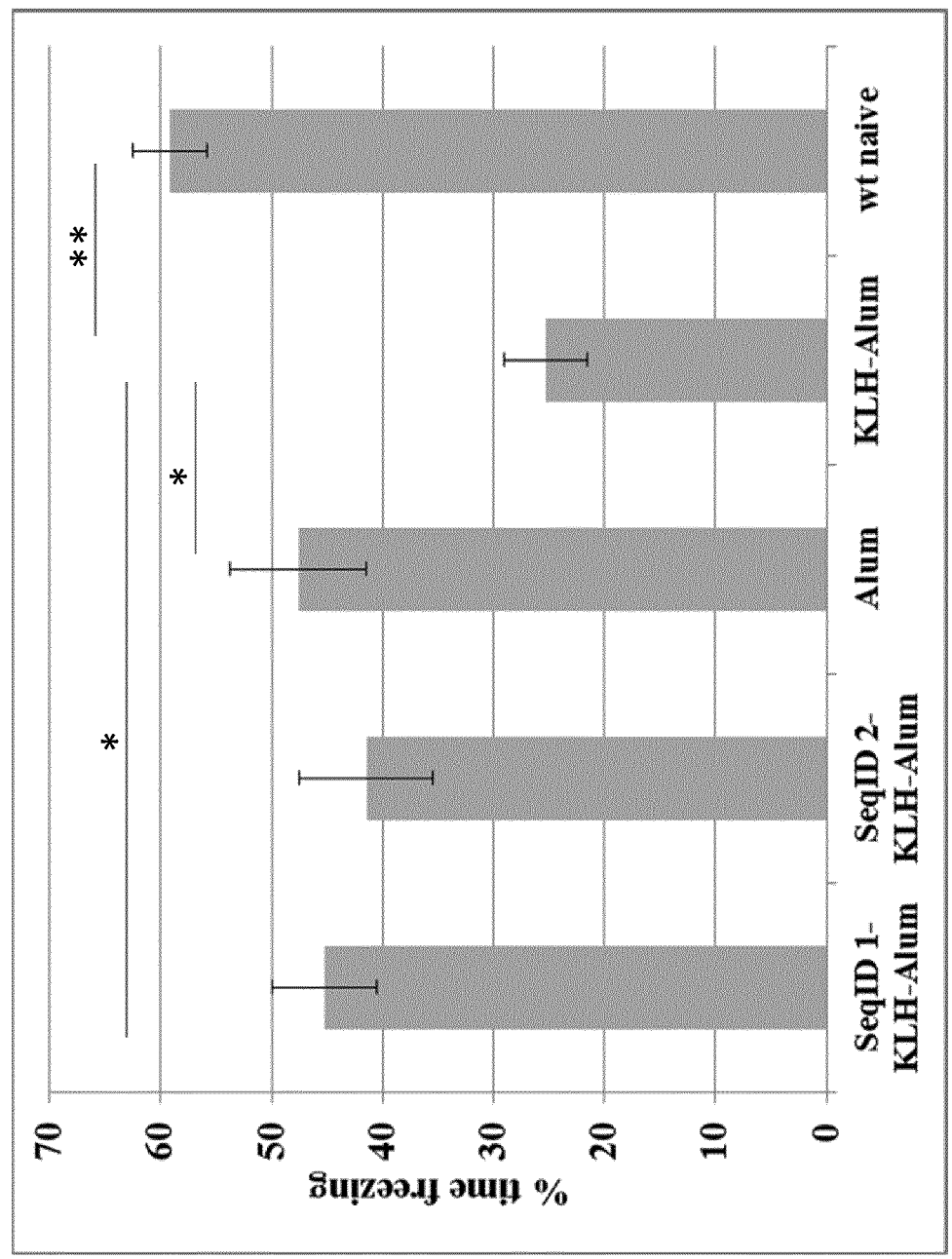

FIG. 7 shows memory and learning of the mice tested: Groups of Tg2576 mice (n≤10/group) received 6 monthly injections of KLH/ALUM (n=9) or SeqID 1-KLH-Alum (n=10)-, SeqID 2-KLH-Alum (n=7)-conjugate vaccines or ALUM only (n=8). Naïve wt animals (n=20) were used as positive controls for Contextual fear conditioning (CFC). Contextual learning and memory was assessed by CFC-analysis using % of time freezing at the end of CFC testing. Parameter depicted is the % of time the animals are 99% immobile during a representative 2-minute period on day two of the CFC testing paradigm. * . . . p<0.05; ** . . . p<0.01.

Figure 8:
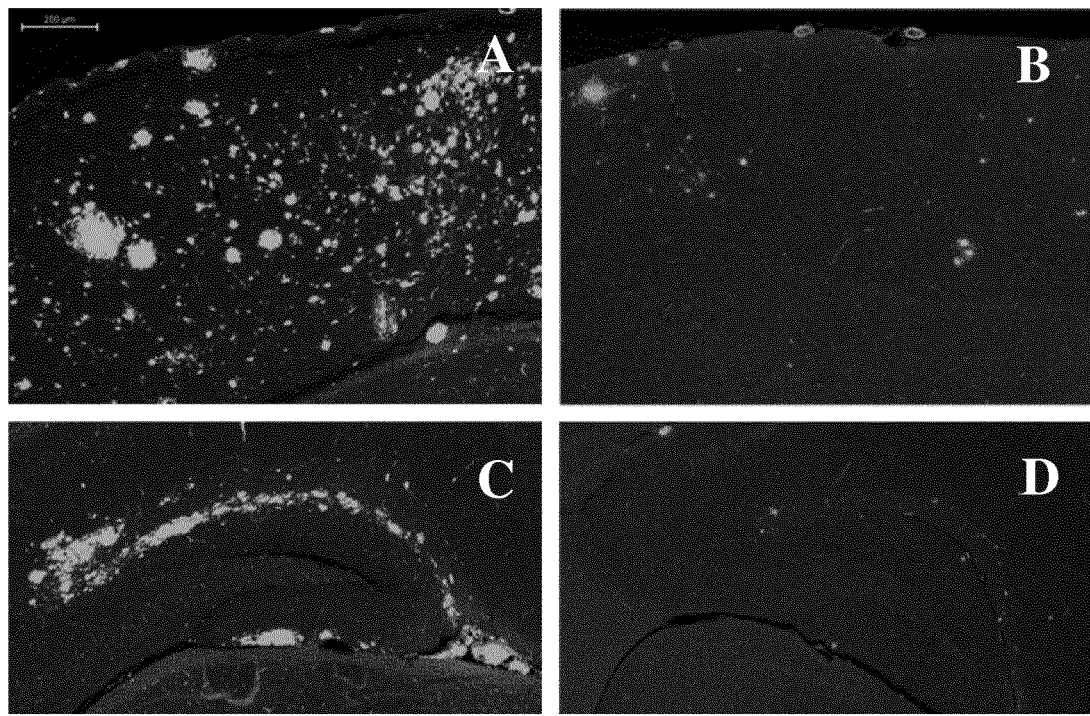
Figure 8:
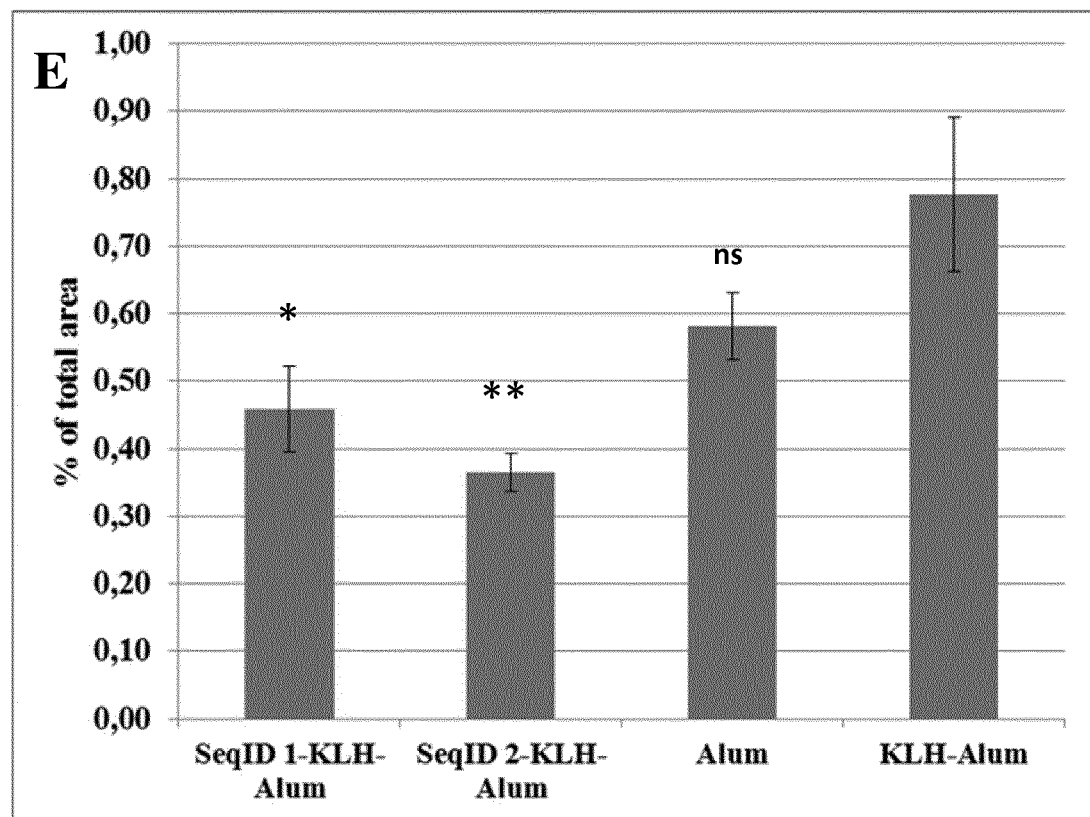

FIG. 8 shows amyloid load in the animals tested: Groups of Tg2576 mice (n≤10/group) received 6 monthly injections of KLH/ALUM (n=9) or SeqID 1 (n=10)-, SeqID 2 (n=7)-conjugate vaccines or ALUM only (n=8). Alum dose in all formulations equivalent to 2 mg/ml. Brains were isolated, 8 weeks after the 6th immunization. Quantification of the relative total brain area covered by amyloid deposits (in % of total tissue analyzed) is based on immuno-fluorescence staining using the Aβ specific mAb 3A5. Representative subregions of the cortex (A, B) and dentate gyrus (C, D) of controls (A, C) and SeqID 1-(B, D) immunized mice are shown. E) SeqID 1-KLH Alum+SeqID 2-KLH Alum reduces the relative area covered by amyloid deposits compared to KLH-Alum controls significantly (diffuse and dense cored amyloid; * . . . p<0.05, ** . . . p<0.01). A slight but insignificant reduction in Aβ deposition is detectable in Alum only treated vs. KLH-Alum treated animals. (ns) Arrowhead in C indicates unspecific fluorescence from a cerebral vessel. Scale bar: 200 µM; pictures taken at 10× magnification.

EXAMPLES

1. Excerpt of an AD clinical trial (AFF006; Eudract: 2009-016504-22)

Materials and Methods:

Data supporting the invention are derived from a randomized clinical trial in early AD patients. The study (AFF006; Eudract: 2009-016504-22) randomized early AD patients into 5 treatment arms. Patients of 2 study arms received either 1 mg aluminium or 2 mg aluminium. In total, 99 early AD patients were enrolled into the 2 study arms. Participation of a given patient lasted 18 months.

Study Design:

AFF006 was conducted as a randomized, placebo-controlled, parallel group, double-blind, multi-center phase II study and assessed the clinical and immunological activity as well as the safety and tolerability of repeated s.c. administrations of i.a. aluminium (different doses) in patients with early AD, as defined in the protocol. It was performed in a total of 6 countries: Austria, France, Germany, Slovakia, Czech Republic and Croatia.

The clinical trial comprised 10 regular outpatient visits and 6 telephone interviews. Up to four weeks before start of treatment, a screening visit (Visit 1) was performed to ensure suitability of the patients for the clinical trial and to establish the patients' baseline characteristics. Following screening, eligible patients were randomly allocated to the treatment groups. After randomization at week 0, patients received 6 injections with either 1 or 2 mg aluminium. Injections were applied s.c. by the investigator at weeks 0, 4, 8, 12, 40 and 65 (Visit 2, 3, 4, 5, 7 and 9).

At Visits 2, 3, 4, 5, 6, 7 and 9 possible local and systemic reactions to the vaccine and vital signs (blood pressure, heart rate, respiratory rate and body temperature) were assessed. In addition, a physical and neurological examination was performed. Efficacy parameters were assessed at Visits 1, 2, 3, 5, 6, 7, 8, 9, 10. The final visit (Visit 10) was performed twelve weeks after the last administration of study drug (Visit 9). An early discontinuation visit (EDV) was performed when a patient discontinued from the clinical trial.

Study Population

The study was done in patients with early AD. Diagnosis was defined by the following criteria:
probable Alzheimer's disease as defined by NINCDS/ADRDA criteria (1)
MMSE score ≥20 (2)
result of Free and Cued Selective Reminding Test (FCSRT) result of total recall ≤40 or free recall ≤17, indicating hippocampal damage impairing the patient's episodic memory (3)
the result of a centrally read MRI of a patient's brain must be compatible with the diagnosis AD, in particular, presence of a medial temporal lobe atrophy (Scheltens Score ≥2) (4)

Other in-/exclusion criteria applied (e.g., written informed consent; age between 50 and 80 years, treatment with immunosuppressive drugs (exclusion)).

Administration of Study Drug

During the study Visits 2, 3, 4, 5, 7 and 9 the patient received study drug by the investigator, in total: six injections over a 65-week treatment period. Injections were applied to the external surface of the upper arm, approximately 8-10 cm above the elbow. Prerequisite regarding the actual site was the presence of an intact regional lymph node station. If the draining lymph node stations of both upper arms were not intact, injection was placed into the thigh close to the inguinal lymph nodes. Two alternating injection sites (e.g. left and right upper arm, left upper arm and left thigh) were used throughout the 6 injections.

Injections were applied to the subcutaneous tissue (s.c.). Special care was taken to avoid intravasal application by careful aspiration before each injection. All administrations were performed at the trial site.

Volume-Based Morphometry

Hippocampus (left and right), and whole lateral ventricle ROIs were delineated on an anatomical MRI template in order to generate the atlas for volumetric measures. The volumes of the hippocampus and lateral ventricles for each subject were determined using a fully-automated method which combines transformations derived from the nonlinear registration of the atlas labels to individual subject scans and subject-specific image information (Collins et al., J. Comput. Assist. Tomogr., 18: 192-205, 1994). Lateral ventricle and hippocampal segmentations that failed post-processing QC review were manually corrected. The total intracranial volume (TIV) was estimated from the brain mask generated during pre-processing and the average TIV ($TIV_{avg}$) for each subject was determined by averaging the estimated TIV across visits. The normalization factor ($TIV_{template}/TIV_{avg\_subject}$) was used to normalize the hippocampal and ventricular volumes for each subject in order to account for differences in head size.

Safety Assessments:

Safety evaluations included the following:
adverse events (AEs) and serious adverse events (SAEs) (number of patients who withdrew due to AEs; reason for withdrawal)
Laboratory assessments: hematology, biochemistry, coagulation, serology, urinalysis, APP crossreactivity
vital signs (blood pressure, heart rate, respiratory rate and body temperature)
physical and neurological examination Efficacy Assessments:

The primary efficacy variables are the change from baseline (CFB) in cognition as measured by an adapted ADAS-cog, CFB in function as measured by an adapted ADCS-ADL and a combination of CFB in cognition and function as measured by a combined composite:
1. Co-Primary: Adapted ADAS-cog;
2. Co-Primary: Adapted ADCS-ADL;
3. Combined Primary Outcome: Composite score.

ADAS-cog and other items included in the adapted ADAS-cog were measured at Visits 1, 2, 3, 5, 6, 7, 8, 9 and 10 or EDV. ADCS-ADL were measured at Visits 2, 5, 6, 7, 8, 9 and 10 or EDV. Items that contributing to the combined primary outcome were measured at Visits 2, 5, 6, 7, 8, 9 and 10 or EDV.

The primary efficacy outcomes all range from 0 to 100. For each adapted scale and composite, a lower score indicates better performance. However, some items included in a scale may be opposite in direction, i.e. a higher score indicates better performance. Before a composite was calculated, contributing items that are scored in the opposite direction were reversed. An item is reversed in score by subtracting the observed value from the maximum possible value for the item. This reverses the scale of the items so that a lower score now indicates better performance. The following items included in the adapted ADAS-cog and combined composite require reverse scoring: Verbal PAL, NTB Category Fluency and CogState ONB.

Secondary Efficacy Outcomes:

Quality of Life (QOL) Caregiver

QOL caregiver is a brief, 13-item questionnaire designed to specifically obtain a rating of the QOL of the patient from the caregiver's perspective. Questions cover relationships with friends and family, concerns about finances, physical condition, mood, and an overall assessment of life quality. All items are rated on a four-point scale, with 1 being poor and 4 being excellent. The total score is the sum of all items, which can range from 13 to 52. QOL caregiver values are presented here as the change from baseline. Outcomes were measured at Visits 1, 6, 8, and 10.

Statistical Analysis

Baseline Data

Subjects were described using demographic information and baseline characteristics recorded during the screening phase (Visit 1).

Demographic information assessed was age, gender, racial group, smoking habits, level of education, height and weight. Subject demographics was summarized by treatment for the Safety, ITT and Per Protocol populations.

Primary Efficacy Analysis

The primary, secondary and exploratory efficacy outcomes were analyzed by comparing change over time between the groups. The efficacy analyses utilized the mixed model described below. The mixed model analysis compared the estimated change from baseline between the 3 vaccine and the 2 aluminium groups in all efficacy outcome scores at each visit. The model used separate repeated measures longitudinal models for each efficacy endpoint. This analysis assessed whether or not there is a difference in estimated CFB values between treatment groups.

SAS• PROC MIXED was used to fit a mixed model with repeated measures (MMRM), with CFB of each of the efficacy outcomes (e.g., Adapted ADAS-cog) as the response variable and the following covariates and fixed effects:

Age (covariate);
Level of Education (fixed effect split into categories of ≤12 years, >12 years);
Gender (fixed effect);
Baseline Test Score of Efficacy Parameter (covariate);
Center (fixed effect);
Treatment (fixed effect);
APOEe4 status (fixed effect, positive or negative);
Use of AChE Inhibitors (fixed effect, determined from medications);
Time (covariate, time will be defined in terms of visits);
Time by Treatment Interaction (Time*Treatment);

The covariance structure for the model was first-order heterogeneous autoregressive (ARH[1]). Least-squares means were estimated at each visit in the study. The LS mean at a particular visit was interpreted as the expected CFB in the efficacy outcome at that time point (Visit) when the specified treatment was administered. Least squares means and standard errors were estimated from the mixed model at each visit and are shown for the various groups.

The adapted ADAS-cog combines items that assess cognitive function. The adapted ADCS-ADL includes items that are sensitive to functional ability. Cognitive skills are expected to decline toward the beginning of the disease and one's ability to perform basic functions are expected to decline later in the disease. The combined primary outcome (referred to herein as "Composite score") combines both the adapted ADAS-cog and adapted ADCS-ADL to create a Composite score that is sensitive to decline in cognitive and basic functions. The following equation is used to derive the combined primary outcome, i.e. combined Composite score:

Combined Composite Score:
=1.67*Word recall+1.35*Orientation+1.42*Word Recognition+0.55*Recall Instructions+0.81*Spoken Language+1.01*Word Finding+5.42*ONB+0.15*VPAL+0.19*Category Fluency+0.28*Belongings+0.35*Shopping+0.23*Hobbies+0.38*Beverage+0.37*Meal+0.23*Current Events+0.26*TV+0.33*Keeping Appointments+0.37*Travel+0.33*Alone+0.35*Appliance+0.49*Clothes+0.36*Read+0.62*Telephone+0.33*Writing The percent contribution of each item to the combined Composite score can be found in Table 1 below:

| Item | Percent Contribution |
| --- | --- |
| ADAS-cog Word Recall | 16.6 |
| ADAS-cog Orientation | 10.8 |
| ADAS-cog Word Recognition | 17.0 |
| ADAS-cog Recall Instructions | 2.8 |
| ADAS-cog Spoken Language | 4.1 |
| ADAS-cog Word Finding | 5.1 |
| CogState One-Back Memory | 8.5 |
| NTB VPAL | 8.5 |
| NTB Category Fluency | 8.5 |
| ADCS-ADL Belongings | 0.8 |
| ADCS-ADL Shopping | 1.4 |
| ADCS-ADL Hobbies | 0.7 |
| ADCS-ADL Beverage | 1.1 |
| ADCS-ADL Meal | 1.5 |
| ADCS-ADL Current Events | 0.7 |
| ADCS-ADL TV | 0.8 |
| ADCS-ADL Keeping Appointments | 1.0 |
| ADCS-ADL Travel | 1.5 |
| ADCS-ADL Alone | 1.0 |
| ADCS-ADL Appliance | 1.4 |
| ADCS-ADL Clothes | 1.5 |
| ADCS-ADL Read | 0.7 |
| ADCS-ADL Telephone | 3.1 |
| ADCS-ADL Writing | 1.0 |

Results

AFF006 recruited a study population reminiscent of early AD patients based on demographic data (Table 2) and data showing the baseline characteristics of the study groups (Table 3).

Both the frequency and the intensity of the local reactions depend on the aluminium dose administered (Table 4). Such local reactions (LR) serve as a measure of the activation of the innate immune response.

Figure 1:
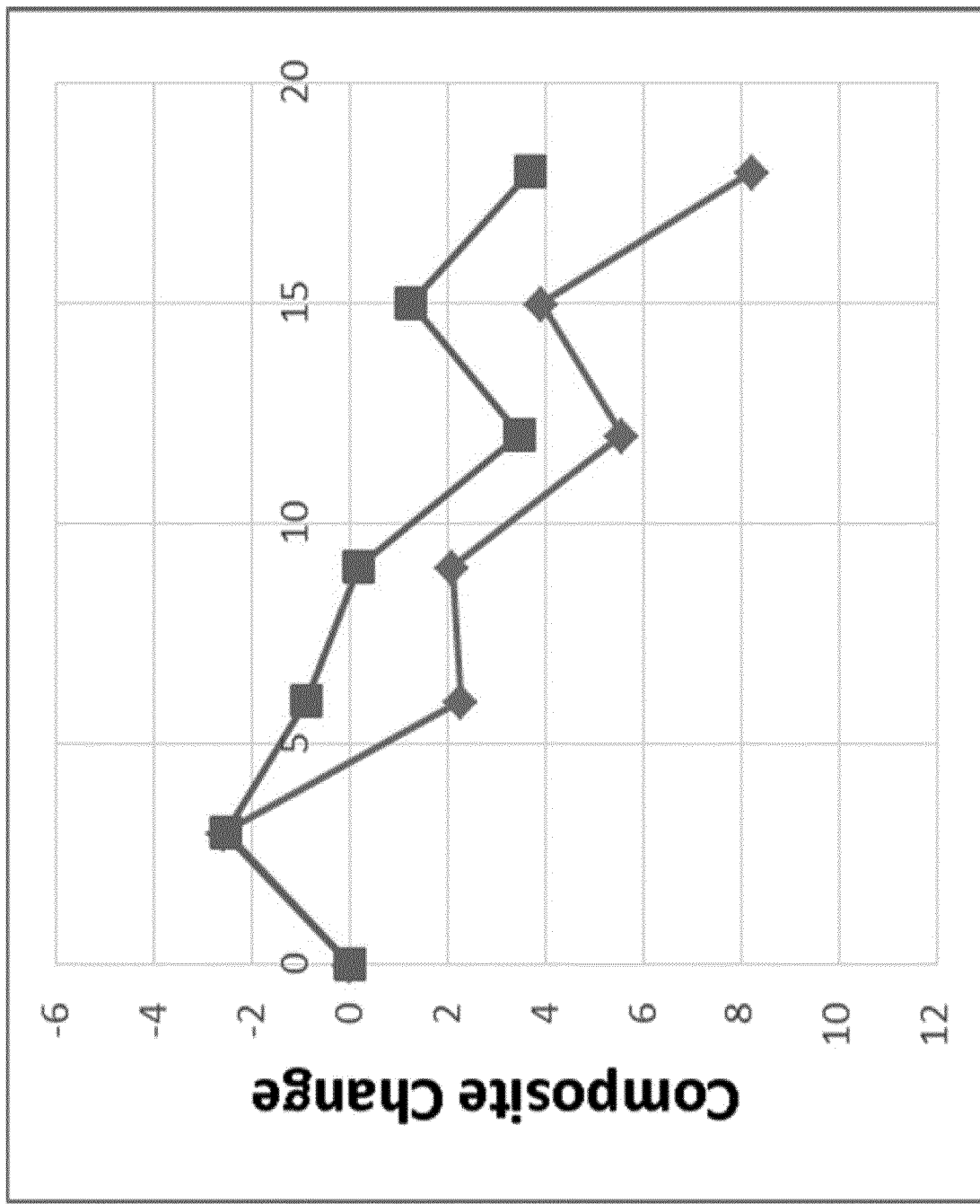
FIG. 1 shows the results of the clinical trial according to the present invention with respect to the change in Composite score composed of (partial) Adapted ADL change and Adapted ADAS-cog change for all patients who have received the 2 mg and 1 mg aluminium oxyhydroxide treatment.
Figure 2:
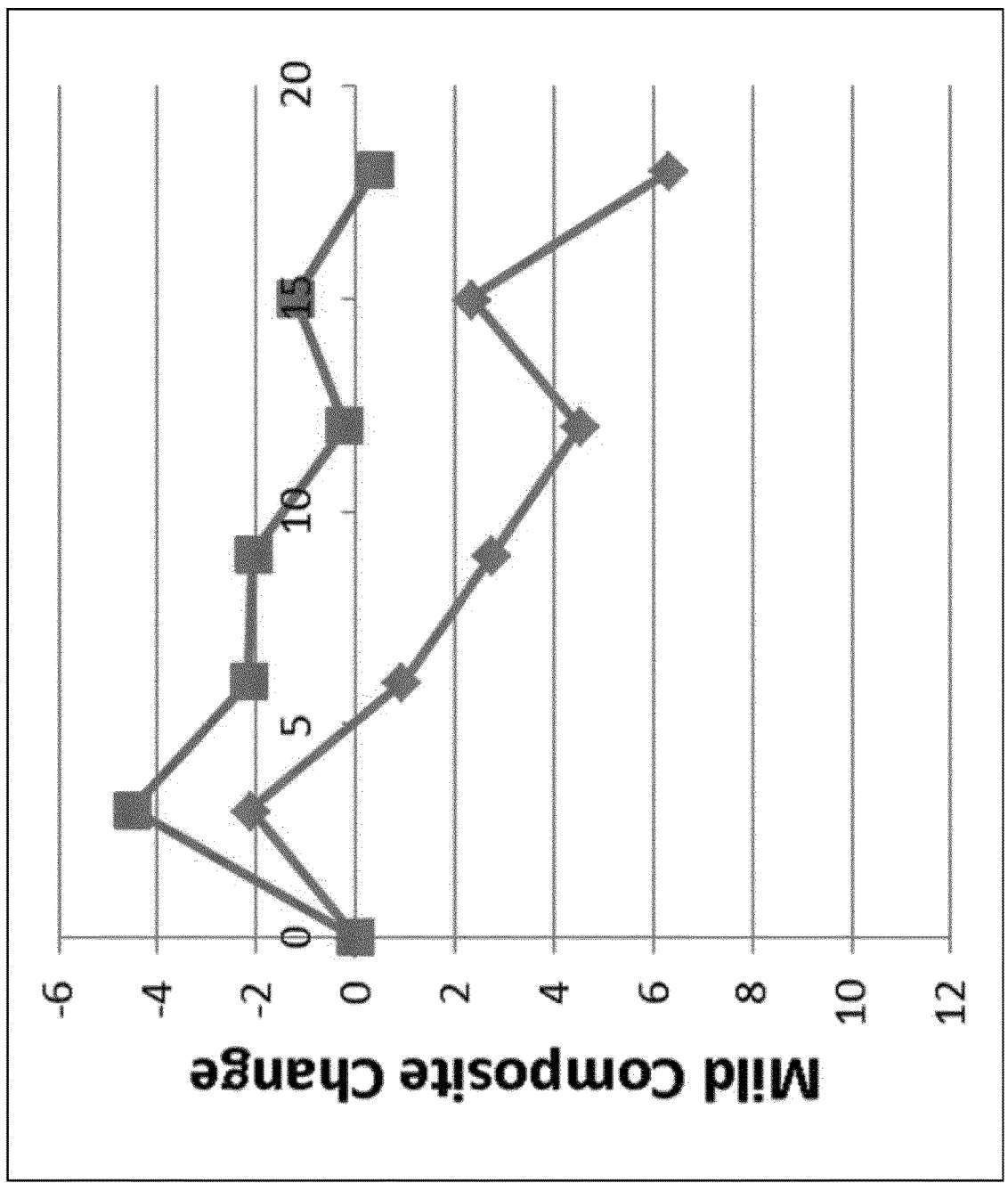
FIG. 2 shows a comparison of the mild population of patients (the mild population is defined by a baseline MMSE score of 24 and higher) of both groups showed that this effect is most pronounced in the cohort of patients in earlier disease stages.

2 mg aluminium group compares favourably even to the 1 mg aluminium group (other groups) with regard to parameters informing on the progression of the disease (FIGS. 1 and 5). Comparison of the mild population of patients of both groups showed that this effect is most pronounced in the cohort of patients in earlier disease stages (FIG. 2). Slowing of disease progression over 18 months is specifically apparent in the 2 mg aluminium group, exemplified with Adapted ADAS-cog (FIG. 3).

Results obtained were compared to public datasets. Historical datasets identified were the ADNI 1 mild AD cohort (observational study), the mild placebo patients from the ADCS Homocysteine trial (HC, MMSE>=20) and the placebo group from the ADCS NSAID study of Rofecoxib and Naproxen (NS, MMSE>=20). These 3 cohorts were combined to yield the historical control (HC-ADNI,NS; HC). Data points were available for 344 patients at month 6, 317 patients at month 12 and 226 patients at month 18. The ADNI trial only performed assessments at 6, 12 and 24 months, so the 18 month value was imputed with a straight line. The NS study was only 12 months long, so no 18 month data was available from this study.

Although the adapted ADAS-cog used some items from the ADAS-cog supplemented with items from the NTB and the CogState Battery, these items were not available for all of the historical studies. So, an adapted ADAS-cog 2 was created which used the same weightings as the adapted ADAS-cog for the ADAS-cog items, but did not include the NTB and CogState items (1.67*Word recall+1.35*Orientation+1.42*Word Recognition+0.55*Recall Instructions+0.81*Spoken Language+1.01*Word Finding).

The adapted ADAS-cog2 shows substantially more decline in the historical control group than the 1 and 2 mg aluminium oxo-hydroxide treated groups from the AFF006 study (FIG. 3). The p-values were: 1 mg vs. HC-ADNI, NS, HC: <0.0001; 2 mg vs. HC-ADNI, NS, HC: <0.0001.

Also the MRI data show a statistically significant disease modifying effect for the 2 mg group of patients and a correlation of the hippocampus volume with clinical endpoints, e.g. right hippocampus with adapADAS: p=0.0006 or Composite score: p=0.0095) (FIG. 4). It has to be specifically mentioned that the present investigation has provided for the first time a parallel development of clinical data with a radiologic biomarker (MRI in the present case)).

FIG. 4 shows that the patients treated according to the present invention showed almost no AD related reduction in hippocampus volume over a period of 18 months whereas the rate of brain atrophy per year in AD patients is in the range of 3 to 6% per year (Risacher et al., 2013, Table 2; the rate in healthy elderly individuals is usually in the range of 0.5 to 2.2 (see also this table 2 in Risacher et al.).

FIG. 5 shows that caregivers of patients treated according to the present invention rated the QOL of the patient as significantly improved over a period of 18 months following 2 mg compared to 1 mg Alum and other groups (not shown).

TABLE 2

Patient Population and Disposition

| Patient Disposition | 1 mg (N = 48) | 2 mg (N = 51) |
|---|---|---|
| Number of Subjects n (%) | | |
| Completed | 41 (85.4%) | 45 (88.2%) |
| Discontinued | 7 (14.6%) | 6 (11.8%) |
| P-value[1] | | |
| Reason for Discontinuation from the Study: | | |
| Death | 2 (4.2%) | 0 (0.0%) |
| Adverse Event | 0 (0.0%) | 0 (0.0%) |
| Withdrawal by Subject | 4 (8.3%) | 5 (9.8%) |
| Lost to Follow-up | 0 (0.0%) | 0 (0.0%) |
| Other | 1 (2.1%) | 1 (2.0%) |

TABLE 3

Demographics—Race, Gender, Education, Age

| Demographics | 1 mg (N = 48) | 2 mg (N = 51) |
|---|---|---|
| Race | | |
| Asian/Pacific Islander | 0 (0.0%) | 1 (2.0%) |
| Caucasian | 48 (100.0%) | 50 (98.0%) |
| Gender | | |
| Male | 28 (58.3%) | 19 (37.3%) |
| Female | 20 (41.7%) | 32 (62.7%) |
| P-value[1] | | |
| Education Years | | |
| Mean (SD) | 12.3 (4.03) | 11.8 (3.18) |
| Median | 12 | 11 |
| (Q1, Q3) | (9.0, 15.0) | (10.0, 13.0) |
| Min, Max | 8, 26 | 6, 22 |
| P-value[1] | | |
| Age (yrs) | | |
| n | 48 | 51 |
| Mean (SD) | 70.3 (6.56) | 68.9 (8.36) |
| Median | 71 | 69 |
| (Q1, Q3) | (65.0, 75.5) | (64.0, 77.0) |
| Min, Max | 57, 80 | 50, 80 |
| P-value[1] | | |
| Weight (kg) | | |
| n | 48 | 51 |
| Mean (SD) | 70.45 (10.375) | 67.62 (13.700) |
| Median | 70.5 | 65 |
| (Q1, Q3) | (64.00, 77.70) | (57.00, 78.00) |
| Min, Max | 47.5, 101.0 | 45.0, 100.0 |
| P-value[1] | | |
| BMI (kg/m$^2$) | | |
| n | 48 | 51 |
| Mean (SD) | 24.66 (2.903) | 24.81 (3.627) |
| Median | 24.8 | 24.2 |
| (Q1, Q3) | (22.95, 26.15) | (22.30, 27.30) |
| Min, Max | 17.8, 31.2 | 18.2, 35.4 |
| P-value[1] | | |

TABLE 4

Adverse Event Summary of Local Reactions

| MedDRA System Organ Class Preferred Term | 1 mg (N = 48) | 2 mg (N = 51) |
|---|---|---|
| Number of subjects with reported adverse event | 31 (64.6%) | 42 (82.4%) |
| Number of unique events | 96 | 162 |
| General Disorders and Administration Site Conditions | 31 (64.6%), 209 | 42 (82.4%), 487 |
| Injection Site Erythema | 26 (54.2%), 64 | 37 (72.5%), 143 |
| Injection Site Swelling | 13 (27.1%), 27 | 26 (51.0%), 86 |
| Injection Site Warmth | 18 (37.5%), 31 | 25 (49.0%), 67 |
| Injection Site Induration | 13 (27.1%), 32 | 14 (27.5%), 34 |
| Injection Site Pain | 14 (29.2%), 41 | 31 (60.8%), 99 |
| Injection Site Pruritus | 4 (8.3%), 5 | 10 (19.6%), 17 |
| Injection Site Nodule | 4 (8.3%), 5 | 11 (21.6%), 31 |
| Injection Site Hypersensitivity | 2 (4.2%), 2 | 4 (7.8%), 9 |
| Injection Site Haematoma | 2 (4.2%), 2 | 1 (2.0%), 1 |
| Injection Site Discolouration | 0 (0.0%), 0 | 0 (0.0%), 0 |
| Injection Site Inflammation | 0 (0.0%), 0 | 0 (0.0%), 0 |
| Injection Site Reaction | 0 (0.0%), 0 | 0 (0.0%), 0 |
| Fatigue | 0 (0.0%), 0 | 0 (0.0%), 0 |
| Feeling Hot | 0 (0.0%), 0 | 0 (0.0%), 0 |
| Hypothermia | 0 (0.0%), 0 | 0 (0.0%), 0 |
| Injection Site Urticaria | 0 (0.0%), 0 | 0 (0.0%), 0 |
| Pyrexia | 0 (0.0%), 0 | 0 (0.0%), 0 |
| Investigations: Lymph Node Palpable | 0 (0.0%), 0 | 0 (0.0%), 0 |
| Investigations: Body Temperature Increased | 0 (0.0%), 0 | 0 (0.0%), 0 |
| Blood and Lymphatic System Disorders: Lymphadenopathy | 0 (0.0%), 0 | 1 (2.0%), 1 |
| Gastrointestinal Disorders: Glossitis | 0 (0.0%), 0 | 1 (2.0%), 1 |
| Gastrointestinal Disorders: Nausea | 0 (0.0%), 0 | 0 (0.0%), 0 |
| Gastrointestinal Disorders: Vomiting | 0 (0.0%), 0 | 0 (0.0%), 0 |
| Nervous System Disorders: Paraesthesia | 0 (0.0%), 0 | 0 (0.0%), 0 |

TABLE 4-continued

Adverse Event Summary of Local Reactions

| MedDRA System Organ Class<br>Preferred Term | 1 mg<br>(N = 48) | 2 mg<br>(N = 51) |
|---|---|---|
| Nervous System Disorders:<br>Dizziness | 0 (0.0%), 0 | 0 (0.0%), 0 |
| Cardiac Disorders: Cyanosis | 0 (0.0%), 0 | 0 (0.0%), 0 |
| Infections and Infestations:<br>Rash Pustular | 0 (0.0%), 0 | 0 (0.0%), 0 |
| Musculoskeletal and Connective<br>Tissue Disorders: Pain in<br>Extremity | 0 (0.0%), 0 | 1 (2.0%), 1 |
| Psychiatric Disorders: Tension | 0 (0.0%), 0 | 0 (0.0%), 0 |
| Vascular Disorders: Haematoma | 0 (0.0%), 0 | 0 (0.0%), 0 |

2. Immunogenicity of two Aβ targeting vaccines SeqID 1-KLH-Alum and SeqID 2-KLH Alum in comparison to KLH-Alum and Alum only

```
SeqIDs:
SeqID NO. 1:
SWEFRTC

SeqID NO. 2:
SEFKHGC
```

Animal Experiments:

All animal experiments were performed in accordance with the Austrian Animal Experiments Act (TVG2012) using Tg2576-mice (Taconic Farms, USA; 12956/SvEvTac). General health was checked by modified Smith Kline Beecham, Harwell, Imperial College, Royal London Hospital, phenotype assessment (SHIRPA) primary observational screen (Rogers D C et al. (1999) Behav Brain Res 105: 207-217). Mice were injected s.c. 6 times in monthly intervals. Blood was taken in regular intervals, plasma prepared and stored until further use. At study end mice were sacrificed, brains were collected and hemispheres separated. One hemisphere was fixed in 4% Paraformaldehyde (PFA, Sigma Aldrich, USA), dehydrated and paraffin-embedded. Brain tissue was sectioned at 7 μM using a sliding microtome (Leitz, Germany) and sections were mounted on Superfrost Plus Slides (Menzel, Germany).

Titer Determination by ELISA:

Standard enzyme-linked immunosorbent assay (ELISA) technology was used to measure levels of vaccine-induced antibodies in plasma and CSF (Mandler M et al. (2012) J Alzheimers Dis 28: 783-794). Substrates used include human (BACHEM, CH) Aβ1-40/42 (at 5 μg/ml), KLH (1 μg/ml) and peptide-Bovine serum albumin (BSA) conjugates (SeqID 1 and SeqID 2, 1 μM). Optical density (OD) was measured at 405 nm using a micro-well reader (Tecan, CH). ODmax/2 was calculated.

Behavioral Tests:

To analyse cognitive dysfunction, immunised Tg2576 animals were subjected to contextual fear conditioning (CFC, Comery T A et al. (2005) J Neurosci 25: 8898-8902), analyzed using AnyMaze software (Stoelting Co, USA). For CFC, on day 1 mice were placed in the conditioning chamber (AFFiRiS AG, Austria), allowed to habituate for 2 min. and received three 0.8 mA foot-shocks in 2 min intervals plus 30 s rest. To assess contextual learning on day 2, animals were readmitted to the chamber and monitored for 5 min. with s120-240 chosen as time frame for analysis (time freezing=lack of movement except for respiration). The first two minutes of day 1 were considered as baseline-freezing which was subtracted from day 2 values.

Analysis of Cerebral Aβ:

Immunofluorescence (IF) analysis was done as described previously (Mandler M et al. (2012) J Alzheimers Dis 28: 783-794). For Aβ-specific IF-staining, brain sections of immunized Tg2576 were processed for analysis of amyloid load using mAb 3A5 (AFFiRiS AG, Austria). All secondary reagents used were obtained from Vector Labs (USA). For IF, sections were mounted and counterstained using DAPI-containing VECTASHIELD-HardSet Mounting Medium. Sections were examined using MIRAX-SCAN (Carl Zeiss AG, Germany). AD-like pathology in animals was assessed by determining the relative cerebral area occupied by amyloid deposits using a semi-automated area recognition program (eDefiniens Architect XD; www.definiens.com, Mandler M. et al (2015) PLoS ONE 10(1): e0115237). For analysis three slides/animal and ≤five individual sections/slide were assessed. Sections carrying tissue artifacts or aberrant staining were excluded. To assess the number of Aβ-positive vessels, 3A5 stained sections (3 slides/animal covering cortex and hippocampus and up to five individual sections per slide) have been analysed. Aβ-positive vessels were manually counted in sub-regions of the cortex as well as in the hippocampus. Number of positive vessels per $mm^2$ was determined.

REFERENCES

Rogers et al., Behav Brain Res 105 (1999): 207-217.
Mandler et al., PLoS ONE 10(1) (2015): e0115237. doi: 10.1371/journal.pone.0115237.
Mandler et al., J Alzheimers Dis 28: 783-794.
Comery et al., J Neurosci 25 (2005): 8898-8902.

Results:

To test the immunogenicity of two Aβ targeting vaccines SeqID 1-KLH-Alum and SeqID 2-KLH Alum in comparison to KLH-Alum and Alum (Aluminium-oxyhydroxide) only, Tg2576-mice were injected 6x, s.c., at 4-week intervals with either conjugate-vaccine containing 30 μg net peptide, equivalent doses of KLH formulated with Alum or Alum only. Alum doses used were equivalent to 2 mg/ml. Vaccination induced Abs were measured in plasma samples taken at sacrification (SeqID 1 (n=10), SeqID 2 (n=8), KLH-Alum (n=10) and Alum only (n=8)). All 3 vaccines elicited strong and comparable IgG titers towards the peptide used for immunization (FIG. 6A). Alum only did not elicit signals above background (FIG. 6A). Both Aβ targeting vaccines, SeqID 1-KLH-Alum and SeqID 2-KLH-Alum, elicited Abs to human Aβ whereas KLH-Alum vaccine and Alum only did not elicit signals above background in treated animals (FIG. 6B).

To evaluate the effect of Aluminum-oxyhydroxide only (Alum) in comparison to Aβ targeting vaccines (SeqID 1-+SeqID 2-KLH-Alum) and non Aβ specific vaccines (KLH-Alum) on cognitive functions, we applied Contextual Fear Conditioning (CFC) analyzing contextual memory and learning in Tg2576-mice. As expected, CFC demonstrated that SeqID 1- and SeqID 2-treated mice were superior to control animals receiving KLH-Alum (thus not eliciting an Aβ specific immune response) in this AD model of Aβ deposition (FIG. 7). Interestingly, animals receiving Alum only, (without a conjugate eliciting an active immune response against KLH or Aβ, respectively), showed similar effects as detectable with Aβ targeting vaccines in this AD model in the absence of Aβ-specific antibodies.

To test whether Alum would also significantly influence cerebral amyloid load, animals undergoing CFC were subsequently sacrificed at 14 months of age. Their brains were assessed for diffuse and dense-cored plaques by IF-staining using monoclonal antibody 3A5. Cortical as well as hippocampal sections of KLH/ALUM-injected controls were covered by numerous amyloid plaques (FIG. 8A+C). By contrast, respective brain areas of SeqID 1- and SeqID 2-immunized Tg2576-mice contained significantly less deposits (FIGS. 8B+D and E, p<0.05 and data not shown). Importantly, treatment of Tg2576 animals with Alum only did not significantly alter amyloid deposition as compared to KLH-Alum treated animals (FIG. 8 E) in this AD model.

Thus, FIGS. 7 and 8 also disclose that topically applied aluminium-oxyhydroxide is able to lower cognitive decline significantly in an APP-transgenic model for Alzheimer's disease (Tg2576) without significantly changing cerebral Aβ levels. This is implying an APP/Aβ independent mechanism underlying beneficial functional effects exerted by aluminium-oxyhydroxide in this AD model and further evidences the lack of scientific plausibility of the "amyloid channel hypothesis".

It follows that the present invention discloses the following individually preferred embodiments:

1. Aluminium salt for use in the treatment and prevention of dementias associated with β-amyloid deposition, preferably Alzheimer's Disease (AD).
2. Aluminium salt according to embodiment 1, wherein the aluminium salt has the general formula $Me_a+Al_b^{3+} An^{c-} \cdot nH_2O$, wherein
   $Me^+$ is $Na^+$, $K^+$, $Li^+$, $Rb^+$, $Cs^+$ or $NH_4+$;
   An is $PO_4^{3-}$, $SO_4^{2-}$, $O(OH)^{3-}$, $O_2^-$ or $OH^-$;
   a is 0, 1, 2, or 3;
   b is 1 or 2;
   c is 1, 2, 3, 4, 5, or 6; and
   n is 0 to 48.
3. Aluminium salt according to embodiment 1 or 2, wherein the aluminium salt is selected from aluminium hydroxide, aluminium oxyhydroxide, aluminium phosphate, or aluminium sulphate.
4. Aluminum salt according to any one of embodiments 1 to 3 in a ready-to-use form to be directly applied to a patient, especially in a prefilled syringe.
5. Aluminium salt according to any one of embodiments 1 to 4, contained in a pharmaceutical preparation.
6. Aluminium salt according to any one of embodiments 1 to 5, contained in a pharmaceutical preparation wherein said preparation contains the aluminium salt as the single effective ingredient.
7. Aluminium salt according to any one of embodiments 1 to 6, contained in a pharmaceutical preparation, wherein said preparation comprises auxiliary substances, especially stabilisators, detergents, antioxidants, complexing agents for mono- or divalent metal ions, carbohydrates and/or buffer substances.
8. Aluminium salt according to any one of embodiments 1 to 7, contained in a pharmaceutical preparation wherein said preparation is sterilised and, optionally, liquid, frozen or lyophilised, preferably liquid.
9. Aluminium salt according to any one of embodiments 1 to 8, contained in a pharmaceutical preparation wherein said preparation is liquid and has a pH of 5 to 9, preferably of 5.5 to 8.0, especially from 6 to 7.5.
10. Aluminium salt according to any one of embodiments 1 to 9, wherein the aluminium salt is present in a medicament as single effective ingredient (active substance).
11. Aluminium salt according to any one of embodiments 1 to 10, wherein the aluminium salt is an aluminium oxyhydroxide suspension, preferably European Pharmacopoeia grade aluminium-oxyhydroxide (monograph 1664), especially Alhydrogel.
12. Aluminium salt according to any one of embodiments 1 to 11, wherein the aluminium salt, preferably aluminium oxyhydroxide, is administered in an amount of at least 1.2 mg (given as $Al_2O_3$ equivalent) to an AD patient.
13. Aluminium salt according to any one of embodiments 1 to 12, wherein the aluminium salt, preferably aluminium oxyhydroxide, is administered in an amount of 1.2 mg to 5.0 mg (given as $Al_2O_3$ equivalent) to an AD patient.
14. Aluminium salt according to any one of embodiments 1 to 13, wherein the aluminium salt, preferably aluminium oxyhydroxide, is administered in an amount of at least 1.5 mg (given as $Al_2O_3$ equivalent) to an AD patient.
15. Aluminium salt according to any one of embodiments 1 to 14, wherein the aluminium salt, preferably aluminium oxyhydroxide, is administered in an amount of 1.5 mg to 5.0 mg, preferably 1.5 to 3.0 mg, especially 1.5 to 2.5 mg, (given as $Al_2O_3$ equivalent) to an AD patient.
16. Aluminium salt according to any one of embodiments 1 to 15, wherein the aluminium salt, preferably aluminium oxyhydroxide, is administered in an amount of 1.6 mg to 2.5 mg, preferably 1.8 to 2.2 mg, especially 1.9 to 2.0 mg, (given as $Al_2O_3$ equivalent) to an AD patient.
17. Aluminium salt according to any one of embodiments 1 to 16, wherein the aluminium salt, preferably aluminium oxyhydroxide, additionally contains one or more stabilisators, especially thiomersal, detergents, antioxidants, complexing agents for mono- or divalent metal ions, especially ethylenediaminetetraacetic acid (EDTA), sugars, sugar alcohols, glycerol, and/or buffer substances, especially TRIS or phosphate buffer substances.
18. Aluminium salt according to any one of embodiments 1 to 17 wherein the aluminium salt, preferably aluminium oxyhydroxide, is administered to a patient in a suspension with a pH of 4 to 10, preferably of 5 to 9, more preferred of 6 to 8, especially from 7.0 to 7.5.
19. Aluminium salt according to any one of embodiments 1 to 18 wherein the aluminium salt, preferably aluminium oxyhydroxide, is administered to a patient in an isotonic suspension.
20. Aluminium salt according to any one of embodiments 1 to 19, wherein the aluminium salt, preferably aluminium oxyhydroxide, is administered subcutaneously, intranodally, intradermally, or intramuscularly, especially subcutaneously, to an AD patient.
21. Aluminium salt according to any one of embodiments 1 to 20, wherein the aluminium salt, preferably aluminium oxyhydroxide, is administered at least once monthly for at least two months to an AD patient.
22. Aluminium salt according to any one of embodiments 1 to 21, wherein the aluminium salt, preferably aluminium oxyhydroxide, is administered at least once monthly for at least six months to an AD patient.
23. Aluminium salt according to any one of embodiments 1 to 22, wherein the aluminium salt, preferably aluminium oxyhydroxide, is administered at least twice a month for at least six months, preferably for at least twelve months, especially at least 24 months, to an AD patient.
24. Aluminium salt according to any one of embodiments 1 to 23, wherein the aluminium salt, preferably aluminium oxyhydroxide, is administered to an AD patient subcutaneously in the upper arm, preferably alternating in the left and in the right upper arm.

25. Aluminium salt according to any one of embodiments 1 to 24, wherein the aluminium salt, preferably aluminium oxyhydroxide, is administered in split doses to an AD patient, especially at the same site of administration.

26. Aluminium salt according to any one of embodiments 1 to 25, wherein the aluminium salt, preferably aluminium oxyhydroxide, is administered in split doses of 0.8 to 5.0 mg, preferably of 1.0 to 3.0, especially from 1.0 to 1.5 mg, (given as $Al_2O_3$ equivalent) to an AD patient.
27. Aluminium salt according to any one of embodiments 1 to 26, wherein the aluminium salt, preferably aluminium oxyhydroxide, is administered at least monthly for at least two years, preferably at least four years, especially at least 8 years, to an AD patient.
28. Aluminium salt according to any one of embodiments 1 to 27, wherein the aluminium salt, preferably aluminium oxyhydroxide, is administered by an injection device, especially a syringe, to an AD patient.
29. Aluminium salt according to any one of embodiments 1 to 28, wherein the aluminium salt, preferably aluminium oxyhydroxide, is administered in an amount of at least 1.8 mg (given as $Al_2O_3$ equivalent) to an AD patient.
30. Aluminium salt according to any one of embodiments 1 to 29, wherein the aluminium salt is preferably aluminium oxyhydroxide and is administered to the AD patient in liquid form in an application volume of 0.1 to 10 ml, preferably of 0.2 to 5 ml, especially of 0.4 to 3 ml.
31. Aluminium salt for use according to any one of embodiments 1 to 30 contained in a pharmaceutical preparation, wherein said preparation is devoid of sulphate, nitrate, or chloride anions.
32. Aluminium salt for use according to any one of embodiments 1 to 31 contained in a pharmaceutical preparation, wherein said preparation has a heavy metal content of less than 20 ppm.
33. Aluminium salt for use according to any one of embodiments 1 to 32 contained in a pharmaceutical preparation, wherein said preparation is a suspension of aluminium oxyhydroxide and has a particle size distribution between 2 μm and approximately 10 μm, said particles being aggregates, composed of smaller fibers of preferably about 2 nm×4.5 nm×10 nm.

The invention claimed is:

1. A method for treating mild cognitive impairment (MCI), comprising:
   administering to a patient diagnosed with an MCI a pharmaceutical formulation comprising a sole active pharmaceutical ingredient, wherein the sole active pharmaceutical ingredient is an aluminum salt in an amount from about 1.0 mg to about 3.0 mg.
2. The method according to claim 1, comprising administering a mini-mental state examination (MMSE) to the patient.
3. The method according to claim 2, wherein the patient has an MMSE score of between 25 and 29 points.
4. The method according to claim 3, wherein the patient has an MMSE score of between 26 and 29 points.
5. The method according to claim 3, wherein the patient has an MMSE score of between 25 and 27 points.
6. The method according to claim 1, wherein the MCI is amnestic MCI, nonamnestic MCI, or early-stage Alzheimer's Disease.
7. The method of claim 1, further comprising:
   diagnosing the patient with the MCI based on identifying the patient as having at least one feature selected from: medial temporal lobe atrophy, temporoparietal cortical hypometabolism, abnormality of cerebrospinal fluid markers comprising tau, amyloid-β42 or phosphorylated-tau, and positivity on amyloid in the patient.
8. The method according to claim 1, further comprising:
   diagnosing the patient with the MCI based on identifying the patient as having atrophy of entorhinal or hippocampal cortex.
9. The method according to claim 1, wherein the aluminum salt has the general formula $Me_a^+Al_b^{3+}An_c^-.nH_2O$, wherein:

Me⁺ is $Na^+$, $K^+$, $Li^+$, $Rb^+$, $Cs^+$ or $NH_4^+$;

An is $PO_4^{3-}$, $SO_4^{2-}$, $O(OH)^{3-}$, $O^{2-}$ or $OH^-$;

a is 0, 1, 2, or 3;

b is 1 or 2;

c is 1, 2, 3, 4, 5, or 6; and n is 0 to 48.

10. The method according to claim 9, wherein the aluminum salt comprises aluminum hydroxide, aluminum oxyhydroxide, aluminum phosphate, or aluminum sulfate.

11. The method according to claim 1, comprising administering the aluminum salt to the patient at least once monthly in a single administration dose of from about 1.5 mg to about 3.0 mg.

12. The method according to claim 11, comprising administering the aluminum salt to the patient in a single administration dose of about 2.0 mg.

13. The method according to claim 1, comprising administering a pharmaceutical formulation comprising the aluminum salt and a pharmaceutically acceptable carrier, diluent or excipient.

14. The method according to claim 13, wherein the pharmaceutical formulation comprises an aluminum oxyhydroxide suspension.

15. The method according to claim 14, wherein the aluminium oxyhydroxide suspension has a particle size distribution between about 2 μm and about 10 μm.

16. The method according to claim 15, wherein the pharmaceutical formulation is substantially devoid of sulfate, nitrate, or chloride anions and has a heavy metal content of less than 20 ppm.

17. The method according to claim 1, comprising administering the aluminum salt to the patient subcutaneously, intranasally, intradermally, or intramuscularly.

18. The method according to claim 1, comprising administering the aluminum salt to the patient subcutaneously in the upper arm.

19. The method according to claim 1, comprising administering the aluminum salt to the patient at least once monthly for at least two years.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Trp Glu Phe Arg Thr Cys
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Glu Phe Lys His Gly Cys
1               5
```